United States Patent
Shin

(10) Patent No.: US 8,905,268 B2
(45) Date of Patent: Dec. 9, 2014

(54) WAX DISPENSER FOR DENTAL TECHNOLOGY AND WAX DISPENSER SYSTEM USING THE SAME

(71) Applicant: Hummer Co., Ltd, Gwangju (KR)

(72) Inventor: Hong-Sub Shin, Gwangju (KR)

(73) Assignee: Hummer Co., Ltd, Gwangju (KR)

( * ) Notice: Subject to any disclaimer, the term of this patent is extended or adjusted under 35 U.S.C. 154(b) by 87 days.

(21) Appl. No.: 13/697,992

(22) PCT Filed: Oct. 19, 2012

(86) PCT No.: PCT/KR2012/008590
§ 371 (c)(1),
(2), (4) Date: Nov. 14, 2012

(87) PCT Pub. No.: WO2013/081297
PCT Pub. Date: Jun. 6, 2013

(65) Prior Publication Data
US 2014/0054319 A1 Feb. 27, 2014

(30) Foreign Application Priority Data

Nov. 28, 2011 (KR) .......................... 10-2011-0124890
Nov. 28, 2011 (KR) .......................... 10-2011-0125144
Nov. 28, 2011 (KR) .......................... 10-2011-0125150
Apr. 9, 2012 (KR) .......................... 10-2012-0036616

(51) Int. Cl.
*B67D 7/80* (2010.01)
(Continued)

(52) U.S. Cl.
CPC ............ *A61C 13/081* (2013.01); *A61C 13/0028* (2013.01); *B65D 83/14* (2013.01)
USPC .......... 222/146.5; 222/394; 433/32; 219/421; 219/426

(58) Field of Classification Search
USPC ........... 222/146.1, 146.2, 146.5, 394; 433/32; 219/227, 236, 243, 421, 426; 141/7, 141/25, 27, 65, 318, 319
See application file for complete search history.

(56) References Cited

U.S. PATENT DOCUMENTS 1,782,681 A * 11/1930 Foss et al. ................. 401/188 R
1,836,029 A * 12/1931 Hutt ............................... 141/25
(Continued)

FOREIGN PATENT DOCUMENTS

JP 2811165 8/1998
KR 2001-0054825 7/2001
(Continued)

OTHER PUBLICATIONS

KR 10-2005-0001892 A—English Translation, Machine Translation Jul. 14, 2014.*

*Primary Examiner* — J. Casimer Jacyna
*Assistant Examiner* — Benjamin R Shaw
(74) *Attorney, Agent, or Firm* — Gardner, Linn, Burkhart & Flory, LLP

(57) ABSTRACT

The invention relates to a wax dispenser for dental technology comprising: a wax reservoir in the shape of a hollow tube which contains a liquid wax therein; a nozzle which is disposed on the front end of the wax reservoir and which is in fluid communication with the wax reservoir; a heater which heats wax to keep wax contained in the wax reservoir in liquid state; an air-pressure supplier which increases the pressure in the wax reservoir by the introduction of air from the outside in a pressurization mode and decreases the pressure in the wax reservoir by the discharge of air to the outside in a depressurization mode; and a dispenser actuator comprising a wax passage which allows the wax reservoir to be in fluid communication with the nozzle, and a passage open/shut device arranged to open and shut the wax passage to discharge wax contained in the wax reservoir through the nozzle in the pressurization mode and to introduce wax from the outside to the wax reservoir through the nozzle in the depressurization mode. Therefore, it is possible to facilitate user's convenience and the work efficiency by charging wax in the wax dispenser in the shape of a pen, by discharging wax according to air pressure and by controlling the discharge of wax precisely.

18 Claims, 19 Drawing Sheets

(51) Int. Cl.
*B65D 83/00* (2006.01)
*A61C 3/00* (2006.01)
*A61C 19/00* (2006.01)
*F27B 14/00* (2006.01)
*A61C 13/08* (2006.01)
*A61C 13/00* (2006.01)
*B65D 83/14* (2006.01)

(56) References Cited

U.S. PATENT DOCUMENTS

| | | | |
|---|---|---|---|
| 3,228,566 A * | 1/1966 | Knox, Jr. | 222/146.5 |
| 3,921,858 A * | 11/1975 | Bemm | 222/146.5 |
| 3,971,492 A * | 7/1976 | Lockwood | 222/146.5 |
| 4,060,180 A * | 11/1977 | Wieland, Jr. | 222/146.5 |
| 4,150,770 A * | 4/1979 | Wieland et al. | 222/146.5 |
| 4,553,935 A * | 11/1985 | Ueno | 433/32 |
| 5,346,394 A * | 9/1994 | DeStefanis | 433/32 |
| 6,255,625 B1 * | 7/2001 | Baschenis | 219/227 |
| 2006/0147875 A1 * | 7/2006 | Ahn | 433/32 |

FOREIGN PATENT DOCUMENTS

| | | |
|---|---|---|
| KR | 20-0288975 | 9/2002 |
| KR | 10-2005-0001892 | 1/2005 |
| KR | 10-2005-0001892 A * | 1/2005 |

* cited by examiner

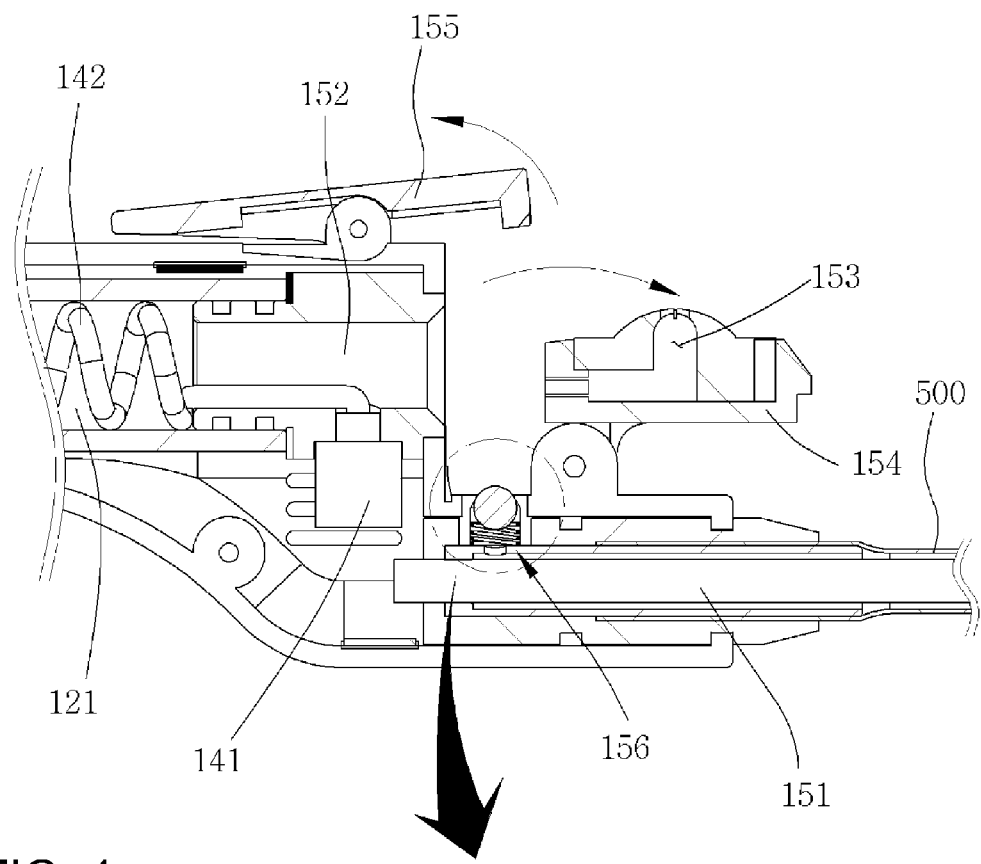
FIG. 4
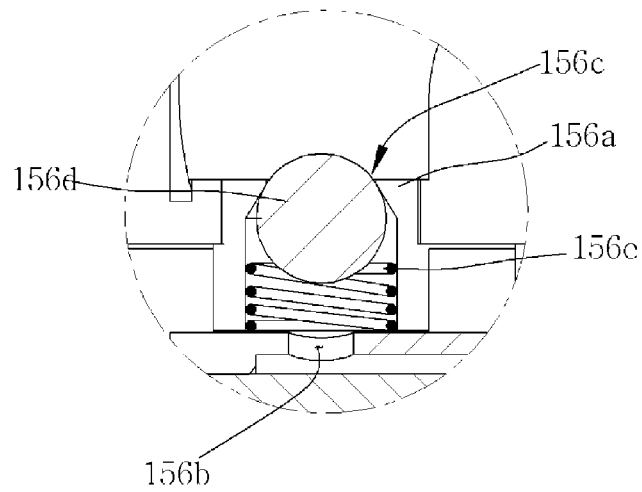

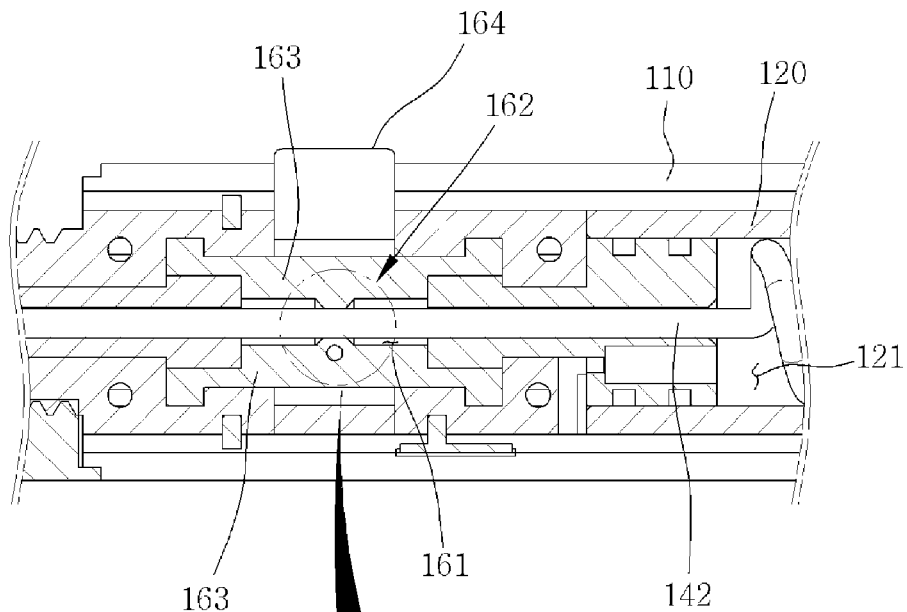
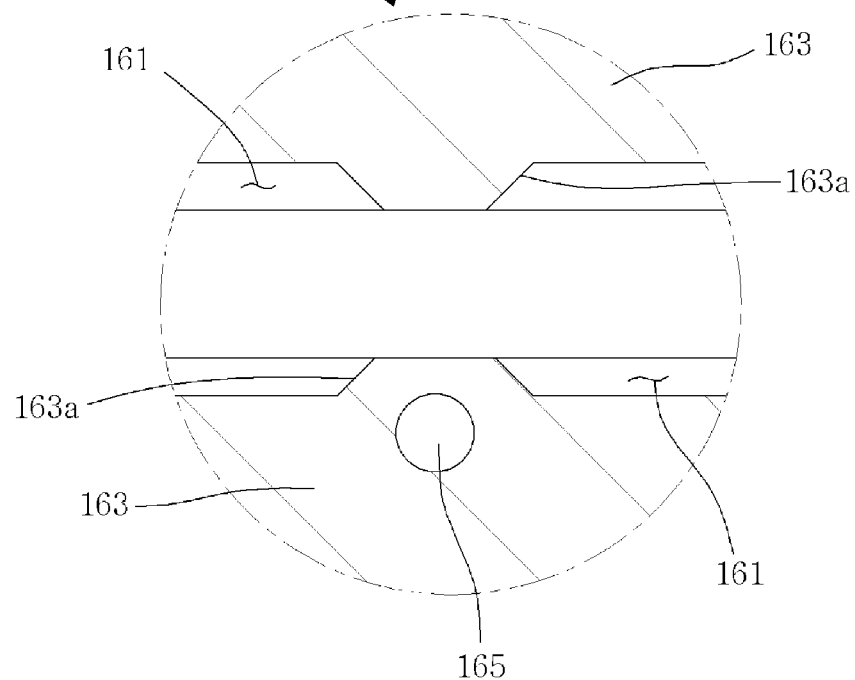
FIG. 5

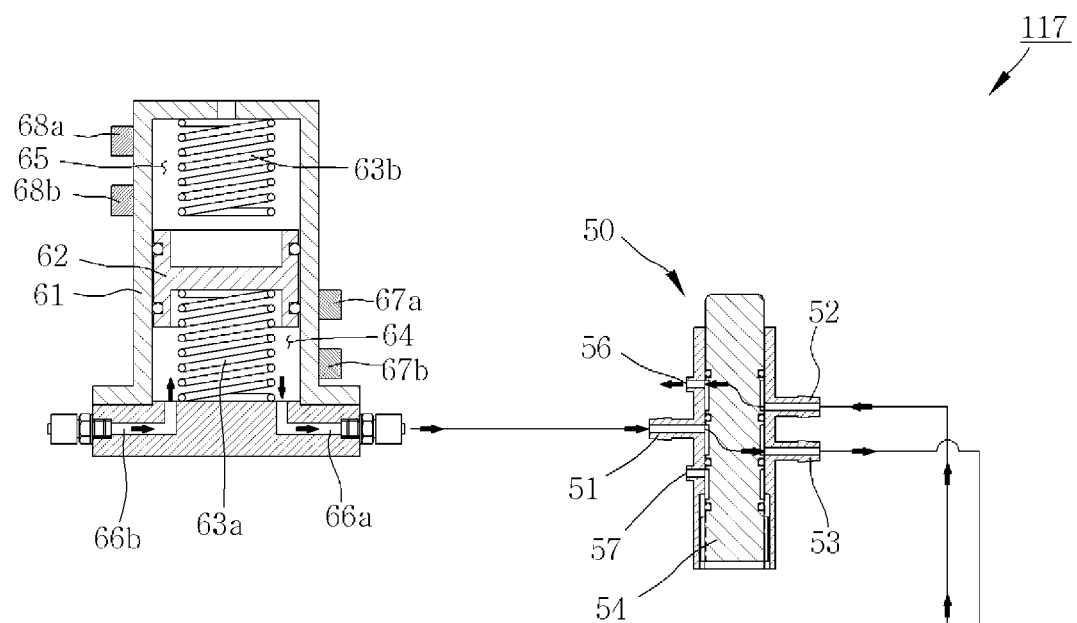
FIG. 8
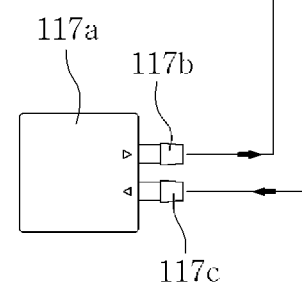

WAX DISPENSER FOR DENTAL TECHNOLOGY AND WAX DISPENSER SYSTEM USING THE SAME

TECHNICAL FIELD

The invention relates to a wax dispenser for dental technology and a wax dispenser system using the same, and in particular relates to the wax dispenser and the wax dispenser system which charges wax in the dispenser and controls the discharge of wax precisely, resulting in the increase of user's convenience and the work efficiency.

BACKGROUND ART

The wax dispenser is a tool for dental technology which is generally used to manufacture false teeth for dental treatment and a tool for coating wax on a plaster cast in the shape of teeth.

Recently, as technologies for dental treatment and material for false teeth develop, there is a growing tendency among people to use false teeth for the dental treatment or beauty. According to this tendency, users who make false teeth such as dental technicians are interested in a wax dispenser for dental technology that ensures the convenience, the increase of work efficiency such as work speed and quality and the safety during the process, and the demand of such a dispenser has been increasing rapidly.

However, in existing technology for the wax dispenser, wax is melted by a tip of the graver heated by alcohol lamp and then wax is applied onto the plaster cast, which makes the work slow and inconvenient.

As disclosed in Japanese patent publication No. 1999-253460, in existing technologies, a solid wax in the form of a rod is inserted into the rear end of the wax dispenser and then is melted by an embedded heater. Therefore, there have been problems during the work such as the leakage of melted wax at the rear end of the wax dispenser due to the inclination of the dispenser or such as the break of a solid wax. Further, for waxing which requires an accurate control, a gun-type tool restricts user's behavior leading to the decrease in product quality.

Moreover, existing technologies do not provide a technique to appropriately maintain the temperature of the wax reservoir of the wax dispenser and the nozzle to which wax is discharged or a technique to control the quantity of wax discharged through the nozzle accurately.

DISCLOSURE OF THE INVENTION

Technical Problem

The invention is provided to solve the above problems and the object of the invention is to facilitate user's convenience and the work efficiency by charging wax into the wax dispenser in the shape of a pen, by discharging wax according to air pressure and by controlling the discharge of wax precisely.

Another object of the invention is to increase user's convenience and the work efficiency by charging wax in the wax dispenser like using a spuit.

It is yet another object of the invention to prevent the blockage of the nozzle due to the solidification of wax or the alteration of wax due to the overheating during the work by making wax discharged through the nozzle heated to proper temperature.

Moreover, it is yet another object of the invention to prevent charged wax from leaking regardless of how the wax dispenser is positioned or inclined, thereby the safety being ensured and user's convenience being improved.

Technical Solution

The object of the invention is achieved by a wax dispenser for dental technology comprising: a wax reservoir in the shape of a hollow tube which contains a liquid wax therein; a nozzle which is disposed on the front end of the wax reservoir and which is in fluid communication with the wax reservoir; a heater which heats wax to keep wax contained in the wax reservoir in liquid state; an air-pressure supplier which increases the pressure in the wax reservoir by the introduction of air from the outside in a pressurization mode and decreases the pressure in the wax reservoir by the discharge of air to the outside in a depressurization mode; and a dispenser actuator comprising a wax passage which allows the wax reservoir to be in fluid communication with the nozzle, and a passage open/shut device arranged to open and shut the wax passage to discharge wax contained in the wax reservoir through the nozzle in the pressurization mode and to introduce wax from the outside to the wax reservoir through the nozzle in the depressurization mode.

Here, the air-pressure supplier may comprise: an outer connection tube which is adapted to introduce air from the outside or to discharge air to the outside; an inner connection tube which is disposed on the rear end of the wax reservoir and which is in fluid communication with the wax reservoir; and an air passage which allows the outer connection tube to be in fluid communication with the inner connection tube.

Also, the wax dispenser may further comprises: a rear cap unit which opens and shuts the rear end of the inner connection tube to make the rear end of the inner connection tube opened or closed, wherein the air passage is disposed in the rear cap unit so that the outer connection tube is made to be in fluid communication with the inner connection tube when the rear cap unit closes the inner connection tube.

Also, the air-pressure supplier may further comprise an air-pressure on/off valve which is adapted to connect the outer connection tube to the air passage and which is adapted to disconnect the outer connection tube from the air passage.

Also, the air-pressure on/off valve may comprise: a valve tube having a first communication hole which is in fluid communication with the air passage and a second communication hole which is in fluid communication with the outer connection tube; an open/shut ball which is contained in the valve tube; and a spring member which is adapted to press the open/shut ball to shut the first communication hole, wherein the open/shut ball closes the first communication hole by the spring force of the spring member when the rear cap unit opens the rear end of the inner connection tube, and the open/shut ball is pressed against the spring force of the spring member by the inner connection tube when the rear cap unit closes the rear end of the inner connection tube such that the open/shut ball opens at least partially the first communication hole to allow the first communication hole to be in fluid communication with the air passage.

Also, the heater may comprise: a heating member which is disposed along the wax passage in the inner space of the wax reservoir; and a heating sleeve which supplies power to the heating member such that the heating member generates heat.

Also, the heating member may extend into the nozzle.

Also, the heating member may be in the shape of a coil spring in the shape of a coil spring in the section where the heating member in the wax reservoir is located.

Also, the passage open/shut device may comprise: an elastic tube which constitutes at least part of the wax passage and which has an elastic contact portion, wherein the elastic contact portion constitutes an inner surface of the elastic tube which is at least partially in contact with an outer surface of the heating member penetrating the wax passage to shut the wax passage; and a side button adapted to press and deform the elastic tube by the external manipulation of the side button such that the elastic contact portion is separated from the heating member and then the wax passage opens.

Alternatively, according to another embodiment, the object of the invention may be achieved by a wax dispenser system for dental technology comprising: a wax dispenser for dental technology; an air cable of which one end is connected to the air-pressure supplier of the wax dispenser for dental technology; and air pumping unit which is connected to the other end of the air cable and which is adapted to discharge air to the air-pressure supplier or to suck air from the air-pressure supplier such that the air-pressure supplier operates in the pressurization mode or the depressurization mode.

Also, the air pumping unit may comprise: an air pump which has a pumping discharge port for the discharge of air and a pumping suction port for the suction of air; and a mode switching valve which selectively connects either the pumping discharge port or the pumping suction port to the air cable.

Also, the mode switching valve may comprise: a cable connection port which is connected to the air cable; a discharge connection port which is connected to the pumping discharge port; a suction connection port which is connected to the pumping suction port; and a valve switch which operates either in a first switching position in which the cable connection port is connected to the discharge connection port for the operation of the air-pressure supplier in the pressurization mode or in a second switching position in which the cable connection port is connected to the suction connection port for the operation of the air-pressure supplier in the depressurization mode.

Also, the mode switching valve may further comprise a first dummy port and a second dummy port which are open to the outside respectively and independently; wherein the valve switch connects the suction connection port to the first dummy port when it operates in the first switching position and connects the discharge connection port to the second dummy port when it operates in the second switching position.

Also, the air pumping unit may further comprise a discharge air-pressure controller disposed on air line which connects the pumping discharge port to the discharge connection port so as to control the pressure of air which is discharged from the air pump.

Also, the wax dispenser system may further comprise: a suction air-pressure controller disposed on air line which connects the pumping suction port to the suction connection port so as to control the pressure of air which is introduced to the air pump.

Also, at least one of the discharge air-pressure controller and the suction air-pressure controller may be configured as an air pressure cylinder which temporarily contains air which is discharged from the air pump or air which is introduced to the air pump and then discharges or sucks air at a predetermined air pressure.

The wax dispenser system may further comprise: a power supply which supplies power for the heat generation of the heater in the wax dispenser for dental technology; and a power cable which connects the power supply to the heater, wherein the power cable extends in the air cable and is connected to the heater.

Here, the wax dispenser system may further comprise: a main body which contains the air pumping unit therein; wherein the main body comprises an air connection port which is connected to the air pumping unit and a power connection port which is connected to the power supply; wherein the wax dispenser system further comprises a connection module which is disposed on the other side of the air cable and which has an air connection jack and a power connection jack, wherein the air connection jack is in fluid communication with the air cable and is connectable to the air connection port, and the power connection jack is electrically connected to the power cable disposed in the air cable and is connectable to the power connection port.

Preferably, the wax dispenser for dental technology according to the second embodiment may comprise: a wax reservoir in the shape of a hollow tube which is made of transparent material and which contains a liquid wax therein; a nozzle in the shape of a hollow tube which is disposed on the front end of the wax reservoir and which is adapted to discharge wax contained in the wax reservoir; a heater which is disposed in the wax reservoir and which keep wax contained in the wax reservoir and wax discharged through the nozzle in liquid state by means of a wire-shaped heating member of which one end is inserted into a hollow part of the nozzle; and a cylinder which discharges wax contained in the wax reservoir by applying air pressure to an inner space of the wax reservoir at the rear end of the wax reservoir and which introduces a liquid wax into the wax reservoir through the nozzle by suction.

Preferably, the cylinder according to the second embodiment may comprise: a cylinder tube which is connected to the rear end of the wax reservoir; a piston which moves in a straight line in the cylinder tube to apply air pressure to the inner space of the wax reservoir; and a motor driving device which moves the piston in a straight line by the rotation force of a motor.

Preferably, the piston according to the second embodiment may comprise: a piston rod which moves forward or backward according to the rotation direction of the motor driving device; a piston head which engages with the piston rod to generate air pressure according to the forward or backward movement of the piston rod; and a diaphragm which is disposed in the piston head and stops the motor driving device when the air pressure in the wax reservoir reaches a predetermined critical value.

Preferably, the cylinder according to the second embodiment may further comprise a first side button which determines the rotation direction of the motor driving device.

Preferably, the cylinder according to the second embodiment may further comprise a backflow preventer cap which transfers air pressure generated by the straight movement of the piston to the inner space of the wax reservoir through a fine hole and which prevents backflow of wax.

Preferably, the wax dispenser according to the second embodiment may further comprise a discharge controller which allows a wax passage to be provided between the wax reservoir and the nozzle and which controls the quantity of wax discharged through the nozzle by opening and closing the wax passage.

Preferably, the discharge controller according to the second embodiment may comprise: an elastic tube which is a hollow tube made of an elastic material and constitutes at least partially the wax passage, wherein an inner surface of the elastic tube is at least partially in close contact with an outer surface of the heating member which penetrates the wax passage and which is inserted into the nozzle; and a second side button which is adapted to supply power to the motor of the motor driving device by the push of the second side button and which is adapted to separate the inner surface of the elastic tube from the heating member by pressing and deforming the elastic tube.

Preferably, the wax dispenser according to the second embodiment may further comprise a housing which contains the wax reservoir and the cylinder therein and which is provided with a window to check the quantity of wax contained in the wax reservoir.

Preferably, a wax dispenser for dental technology according to the third embodiment may comprise: a wax reservoir which is a hollow elastic tube and contains a liquid wax therein; a press button which is adapted to apply pressure to the wax reservoir by user's push of the press button; a nozzle which engages with the front end of the wax reservoir and discharges wax contained in the wax reservoir when the inner pressure of the wax reservoir exceeds a predetermined critical value by the pressure generated by the press button; and a heater which transfers heat to a heat conductor disposed in the wax reservoir and the nozzle to keep wax contained in the wax reservoir and wax discharged through the nozzle in liquid state.

Preferably, the nozzle according to the third embodiment may comprise: a nozzle valve which blocks wax contained in the wax reservoir when the inner pressure of the wax reservoir is lower than a predetermined critical value and which allows wax contained in the wax reservoir to pass when the inner pressure of the wax reservoir is greater than a predetermined critical value; and a nozzle tube to discharge wax which passed through the nozzle valve.

Preferably, the nozzle valve according to the third embodiment may comprise: a wax blocking ball in the shape of a ball; a valve tube which contains the wax blocking ball therein, wherein one end of the valve tube is provided with an inlet into which wax contained in the wax reservoir is introduced and the other end of the valve tube is provided with an outlet which discharges wax to the nozzle tube; and a spring member which presses the wax blocking ball against the inlet in the valve tube to block the inlet.

Preferably, the wax dispenser according to the third embodiment may further comprise: a charge button which is adapted to separate the wax blocking ball from the inlet by user's push of the charge button when a negative pressure is generated in the wax reservoir by the elastic force of the wax reservoir, thereby introducing a liquid wax into the wax reservoir through the nozzle by suction.

Preferably, the charge button according to the third embodiment may comprise: a ball support rod which moves forward or backward in the wax reservoir and supports the wax blocking ball during the forward movement to separate the wax blocking ball from the inlet; and a push button which moves the ball support rod forward by user's push of the push button.

Preferably, the ball support rod according to the third embodiment may be inserted in an insertion hole formed on the rear end of the wax reservoir such that the front end is disposed inside the wax reservoir and the rear end is disposed outside the wax reservoir, and wherein the push button engages with the rear end of the ball support rod to move the ball support rod forward by user's push of the push button.

Preferably, the press button according to the third embodiment may comprise: a side button which is in contact with the outer surface of the wax reservoir and transfers the pressure generated by user's push of the side button to the wax reservoir; and a side button case made of an insulating elastic material which supports the side button such that the side button becomes in contact with the outer surface of the wax reservoir.

Advantageous Effect

According to the invention, it is possible to facilitate user's convenience and the work efficiency by charging wax into the wax dispenser in the shape of a pen, by discharging wax according to the pressure of air discharged from the air pumping unit, and by controlling the discharge of wax according to the dispenser actuator precisely.

Also, it is possible to increase user's convenience and the work efficiency by the suction of the air pumping unit to charge wax into the wax dispenser and by the immersion of the nozzle of the wax dispenser into the wax tank and the suction of wax like a spuit when charged wax is ran out of.

Further it is possible to prevent the blockage of the nozzle due to the solidification of wax or the alteration of wax due to the overheating during the work by making wax discharged through the nozzle heated to proper temperature.

Further, it is possible to prevent charged wax from leaking regardless of how the wax dispenser is positioned or inclined, thereby the safety being ensured and user's convenience being improved.

BRIEF DESCRIPTION OF THE DRAWINGS

FIGS. 3 and 4 represent an enlarged view of an air-pressure supplier of the wax dispenser for dental technology of FIG. 2.

FIG. 5 represents an enlarged view of an open/shut device of the wax dispenser for dental technology of FIG. 2 and a working section thereof.

FIGS. 8 and 9 represent another example of air pumping unit of the wax dispenser system for dental technology according to the first embodiment of the invention.

Figure 1:
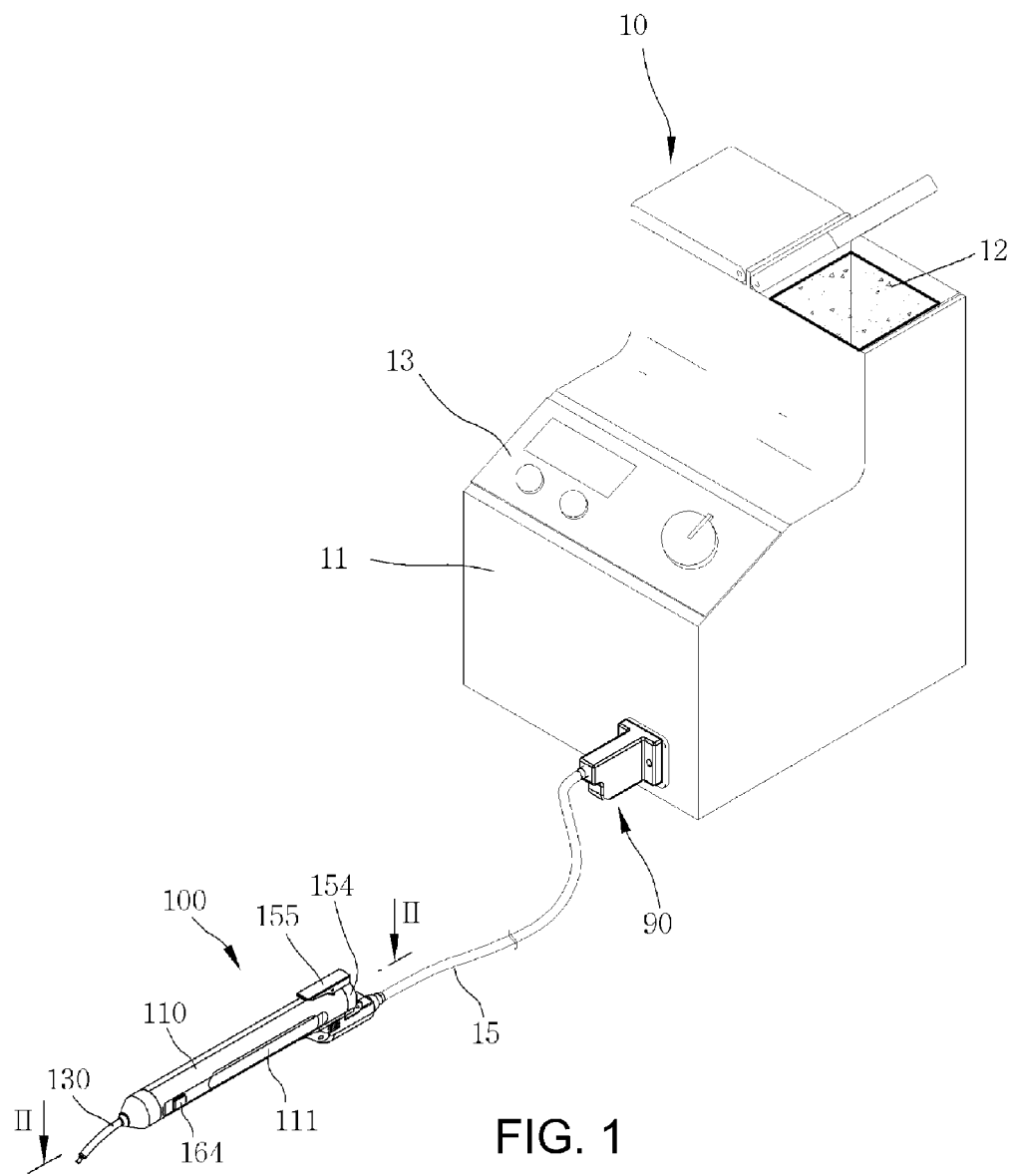
FIG. 1 represents a wax dispenser system for dental technology according to a first embodiment of the invention.

| * List of Reference Numeral | |
|---|---|
| 100: wax dispenser | 110: housing |
| 120: wax reservoir | 130: nozzle |
| 140: heater | 141: heating sleeve |
| 142: heating member | 150: air-pressure supplier |
| 151: outer connecting tube | 152: inner connecting tube |
| 153: air passage | 154: rear cap unit |
| 155: hook-fixing member | 156: air-pressure open/shut valve |
| 160: dispenser actuator | 161: wax passage |
| 162: passage open/shut device | 163: elastic tube |
| 163a: elastic contact portion | 164: side button |
| 165: through hole | 20: mode switching valve |
| 21: cable connection port | 22: discharging connection port |
| 23: suction connection port | 24: valve switch |
| 25: control lever | 26: second dummy port |
| 27: first dummy port | 30: discharge air-pressure controller |
| 40: suction air-pressure controller | |

BEST MODE FOR CARRYING OUT THE INVENTION

Preferably, the invention provides a wax dispenser for dental technology comprising: a wax reservoir in the shape of a hollow tube which contains a liquid wax therein; a nozzle which is disposed on the front end of the wax reservoir and which is in fluid communication with the wax reservoir; a heater which heats wax to keep wax contained in the wax reservoir in liquid state; an air-pressure supplier which increases the pressure in the wax reservoir by the introduction of air from the outside in a pressurization mode and decreases the pressure in the wax reservoir by the discharge of air to the outside in a depressurization mode; and a dispenser actuator comprising a wax passage which allows the wax reservoir to be in fluid communication with the nozzle, and a passage open/shut device arranged to open and shut the wax passage to discharge wax contained in the wax reservoir through the nozzle in the pressurization mode and to introduce wax from the outside to the wax reservoir through the nozzle in the depressurization mode.

Mode for Carrying Out the Invention

The preferred embodiments of the present invention will now be described in detail with reference to the attached drawings, to provide solutions for the above problems. If explanations about prior arts makes the invention unclear, they will not be described. Terms are defined in light of the function of the invention and they may differ according to the inventor's or manufacturer's intention or the practice. Therefore, the definition of terms may be made on the basis of the whole description of the invention.

First Exemplary Embodiment

FIG. 1 represents a wax dispenser system for dental technology according to a first embodiment of the present invention. As shown in FIG. 1, the wax dispenser system for dental technology comprises a wax dispenser 100 for dental technology (hereinafter referred to as "wax dispenser 100"), an air cable 15 and an air pumping unit 116. The air pumping unit 116 is disposed within a main body 10.

The wax dispenser 100 is in the shape of a pen as shown in FIG. 1 and comprises constitutional elements therein. As such, the wax dispenser 100 is embodied in the form of a pen and thus a user is able to grip the dispenser during the work or production of false teeth, which facilitates the operation of the dispenser. The wax dispenser 100 is connected to a main body 10 via an air cable 15, and the dispenser is able to discharge wax when internal pressure is increased by an air pumping unit disposed in the main body 10 or the dispenser is able to suck or draw in, i.e., charge, wax when the internal pressure is decreased by an air pumping unit, which will be discussed in more detail below.

Hereinafter, the wax dispenser 100 according to the first embodiment will be explained in detail referring to FIGS. 2 to 5.

Figure 2:
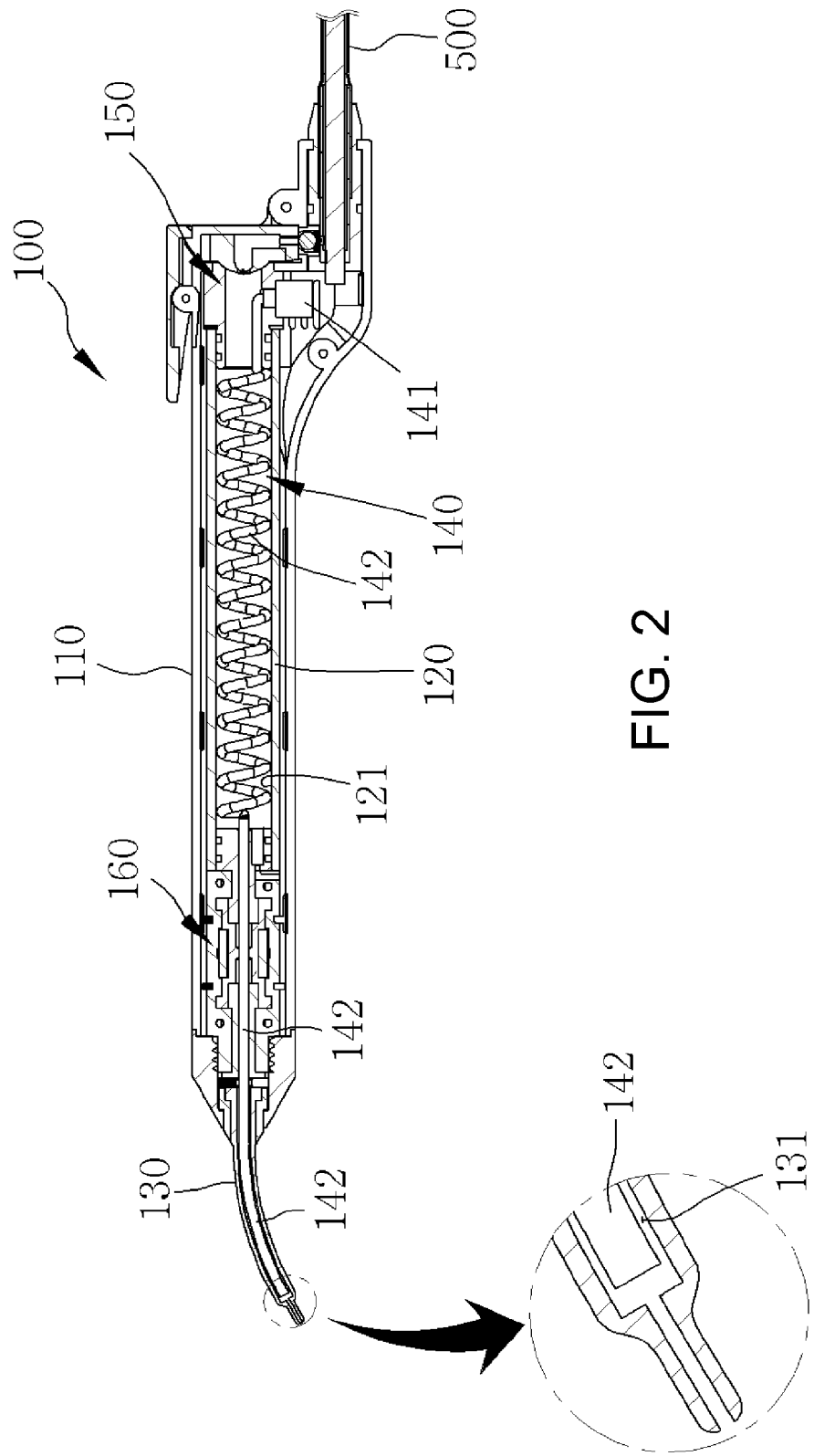
FIG. 2 represents a sectional view taken along the line II-II of FIG. 1 of the wax dispenser for dental technology according to the first embodiment of the invention.

As shown in FIG. 2, the wax dispenser 100 comprises a wax reservoir 120, a nozzle 130, a heater 140, an air-pressure supplier 150 and a dispenser actuator 160. These elements of the wax dispenser 100 such as the wax reservoir 120, the nozzle 130, the heater 140, the air-pressure supplier 150, the dispenser actuator 160, etc., are disposed within a housing 110 which is in the shape of a pen.

The wax reservoir 120 is in the shape of a hollow tube in which wax in liquid state is contained. The wax reservoir 120 extends along the length of the housing 110, i.e., according to the horizontal line in FIG. 2, in the center region of the housing 110. The nozzle 130 is located on the front end of the wax reservoir 120 (left in the FIG. 2) and the air-pressure supplier 150 is located on the rear end of the wax reservoir 120.

The heater 140 applies heat to wax contained in the wax reservoir 120 such that wax remains in the liquid state. In one example, the heater 140 comprises a heating member 142 and a heating sleeve 141, as shown in FIG. 2.

The heating sleeve 141 supplies power to the heating member 142 so that the heating member 142 generates heat. The heating sleeve 141 is provided with power by means of a power supply (not shown) of the main body 10 via a cable 15b, which will be discussed in more detail below.

The heating member 142 is disposed along an inner space 121 of the wax reservoir 120 and along a wax passage 161 in a dispenser actuator 160.

In one example, as shown in FIG. 2, the heating member 142 is in the shape of a coil spring and is arranged within the section where the inner space 121 of the wax reservoir 120 occupies, and the shape of a coil spring allows the heating area of the heating member 142 to be enlarged, thereby enhancing the efficiency to apply heat to wax.

Further, the heating member 142 may extend to an inner part 131 of the nozzle 130 as shown in the enlarged view in FIG. 2. Therefore, a liquid wax contained in the wax reservoir 120 is heated by the heating member 142 which extends along a wax passage 161 of the dispenser actuator 160 when wax moves along the wax passage 161, and also wax is heated by the heating member 142 which is extended to the inner part of the nozzle 130 until it moves to the nozzle 130 and then was is discharged from the nozzle 130, thereby preventing liquid wax from being solidified before the discharge.

Also, if the wax dispenser 100 is not in use, i.e., if the power of the heater 140 is off, wax which remained in the nozzle 130 is solidified over time. But, if the heater 140 begins to work, the heating member 142 in the nozzle 130 allows the solidified wax in the nozzle 130 to turn into a liquid wax, so that wax is able to be used without any other measures.

The air-pressure supplier 150 is located on the rear end of the wax reservoir 120, as described above. The air-pressure supplier 150 operates in one of the two modes: a pressurization mode that increases pressure in the inner space 121 of the wax reservoir 120 and a depressurization mode that decreases pressure in the inner space 121 of the wax reservoir 120.

Specifically, the air-pressure supplier 150 applies pressure to the inner space 121 of the wax reservoir 120 by air which is introduced from the air pumping unit 116, i.e., compressed air, via the air cable 15, and reduces pressure from the inner space 121 of the wax reservoir 120 by air which outflows to the air pumping unit via the air cable 15.

In the pressurization mode, when the air pressure in the inner space 121 of the wax reservoir 120 increases by the compressed air, the dispenser actuator 160 allows the wax reservoir 120 to be in fluid communication with the nozzle 130, and then wax contained in the wax reservoir 120 is discharged to the outside via the nozzle 130. On the contrary, in the depressurization mode, when the pressure in the inner space 121 of the wax reservoir 120 decreases by the outflow of air through the air-pressure supplier 150, the dispenser actuator 160 allows the wax reservoir 120 to be in fluid communication with the nozzle 130, and then wax from the outside is introduced into the wax reservoir 120 through the nozzle 130.

Figure 3:
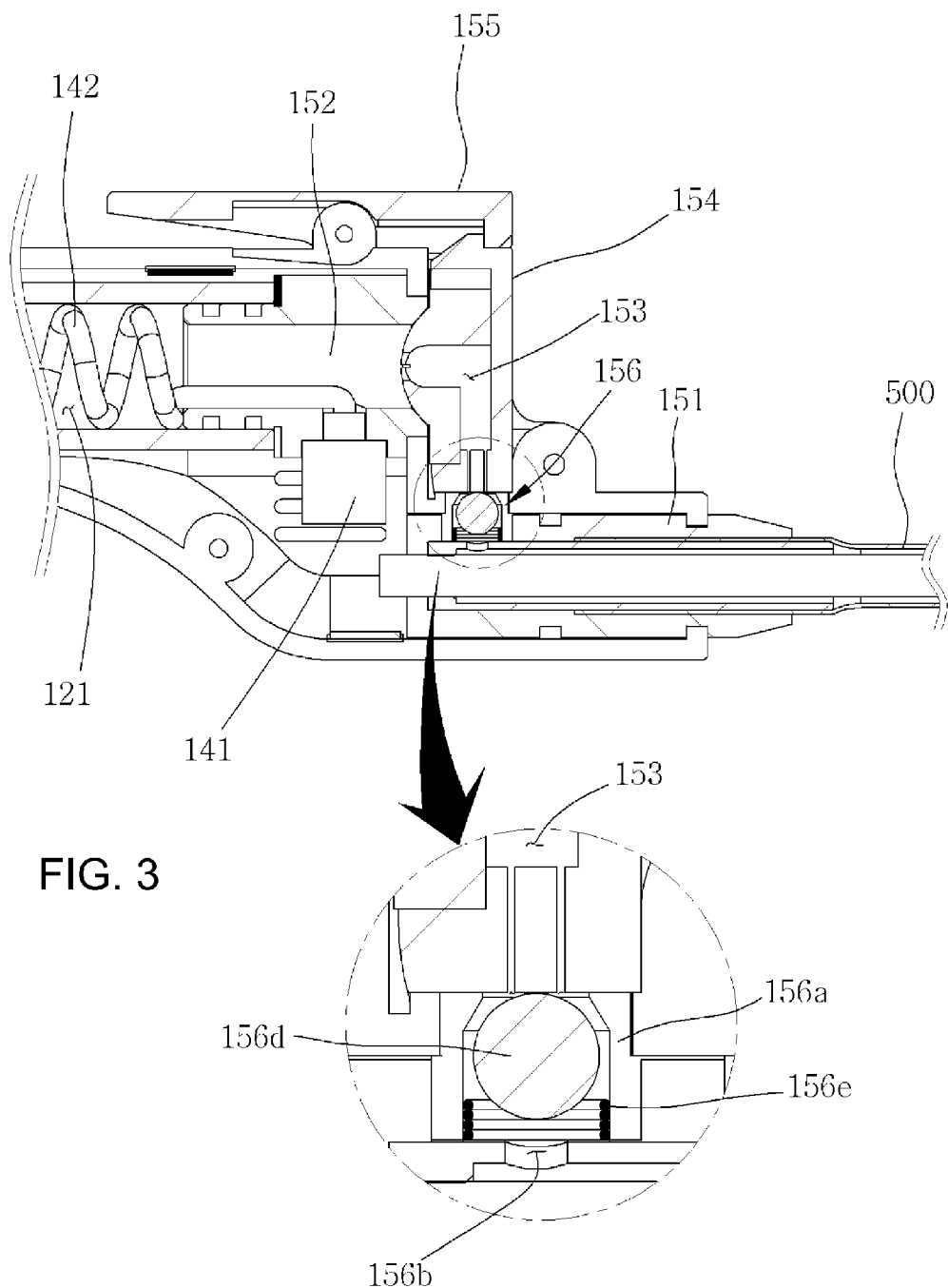

FIGS. 3 and 4 represent an enlarged view of the air-pressure supplier 150 of the wax dispenser 100 according to the invention. Referring to FIGS. 3 and 4, the air-pressure supplier 150 comprises an outer connection tube 151, an inner connection tube 152 and an air passage 153.

The outer connection tube 151 is connected to the air cable 15 such that air is introduced from the outside of the wax dispenser 100, i.e., from the air cable 15, or air is discharged into the air cable 15. The inner connection tube 152 is disposed on the rear end of the wax reservoir 120 to be in fluid communication with the wax reservoir 120.

The air passage 153 allows the outer connection tube 151 to be in fluid communication with the inner connection tube 152, such that air is able to flow from the air cable 15 to the wax reservoir 120 via the outer connection tube 151, the air passage 153, and the inner connection tube 152.

As shown in FIGS. 3 and 4, the wax dispenser 100 according to the invention may comprise a rear cap unit 154 which opens the rear part of the inner connection tube 152 to the outside or closes off the rear part of the inner connection tube 152. FIG. 3 shows that the rear cap unit 154 closes the rear part of the inner connection tube 152 and FIG. 4 shows that the rear cap unit 154 opens the rear part of the inner connection tube 152.

In one example, the air passage 153 according to the invention is provided inside of the rear cap unit 154 and as shown in FIG. 3, the air passage 153 allows the outer connection tube 151 to be in fluid communication with the inner connection tube 152 when the rear cap unit 154 closes the rear part of the inner connection tube 152.

In one example, the rear cap unit 154 is hinged at the rear part of the housing 110 and pivots to open and close the rear part of the inner connection tube 152. The rear cap unit 154 may be fixed by means of a hook-fixing member 155 while it is closing the rear part of the inner connection tube 152.

The air-pressure supplier 150 according to the invention may comprise an air-pressure on/off valve 156 which allows or stops the fluid communication of the outer connection tube 151 with the air passage 153 of the rear cap unit 154. In one example, the air-pressure on/off valve 156 according to the invention may comprise a valve tube 156a, an open/shut ball 156d and a spring member 156e.

The valve tube 156a is disposed between the outer connection tube 151 and the rear cap unit 154 to allow the outer connection tube 151 to be in fluid communication with the air passage 153 of the rear cap unit 154. The valve tube 156a is provided with a first communication hole 156c which is in fluid communication with the air passage 153 and a second communication hole 156b which is in fluid communication with the outer connection tube 151.

The open/shut ball 156d is in the shape of a ball and is received in the valve tube 156a. The spring member 156e applies pressure to the open/shut ball 156d such that the ball 156d shuts the first communication hole 156c. The open/shut ball 156d shuts the first communication hole 156c by the spring force of the spring member 156e when the rear cap unit 154 opens the rear part of the inner connection tube 152 as shown in FIG. 4. Therefore, even when the rear cap unit 154 is opened during the inflow of the compressed air from the air pumping unit 116 via the outer connection tube 151, the compressed air is not discharged to the outside through the first communication hole 156c and thus prevents noise due to the discharge of the compressed air.

Meanwhile, as shown in FIG. 3, when the rear cap unit 154 closes the rear part of the inner connection tube 152, the rear cap unit 154 presses the open/shut ball 156d against the spring force of the spring member 156e such that the first communication hole 156c is opened at least in part. Therefore, the first communication hole 156c is in fluid communication with the air passage 153 such that compressed air can be introduced to the inner connection tube 152 or air can be sucked through the inner connection tube 152.

Hereinafter, the dispenser actuator 160 according to the invention will be described in detail referring to FIG. 5.

The dispenser actuator 160 according to the invention comprises a wax passage 161 which allows the wax reservoir 120 to be in fluid communication with the nozzle 130. The dispenser actuator 160 comprises a passage open/shut device 162 and the passage open/shut device opens and shuts the wax passage 161 such that wax contained in the wax reservoir 120 is discharged to the outside through the nozzle 130 in the pressurization mode and wax is introduced into the wax reservoir 120 through the nozzle 130 from the outside in the depressurization mode.

Therefore, if the wax passage 161 is opened in the pressurization mode by the actuation of the passage open/shut device 162, wax contained in the wax reservoir 120 is sent to the nozzle 130 through the wax passage 161 and thus it is ready for the work using wax. Also, if the wax passage 161 is opened by the actuation of the passage open/shut device 162 in the depressurization mode and then the nozzle 130 is inserted into a wax tank 12, the wax reservoir 120 is filled with wax through the nozzle 130.

The passage open/shut device 162 according to the invention may comprise an elastic tube 163 and a side button 164 as shown in FIG. 5.

The elastic tube 163 constitutes at least part of the wax passage 161. The elastic tube 163 has an elastic contact portion 163a which shuts the wax passage 161 and the elastic contact portion 163a is an inner surface of the elastic tube which is at least partially in contact with an outer surface of the heating member 142 which penetrates through the wax passage 161.

In one example, the elastic tube 163 is made of material such as silicone which is elastically deformable by the actuation of the button 164.

The external manipulation of the side button 164 will press and deform the elastic tube 163 such that the elastic contact portion 163a is separated from the heating member 142 and then the wax passage 161 opens. In one example, the side button 164 is in contact with the outer surface of the elastic tube 163 and the button is exposed at one side to the outside of the housing 110 as shown in FIG. 1.

According to the arrangement described above, if a user pushes the side button 164 which is exposed to the outside of the housing 110, the side button 164 presses and deforms the elastic tube 163 and thus the elastic contact portion 163a is separated from the heating member 142 to open the wax passage 161.

In one example, as shown in the enlarged view of FIG. 5, a through hole 165 which penetrates the elastic tube 163 and the side button 164 is provided and a transmission member is inserted into the through hole 165 such that the push of the side button 164 has an effect on the elastic tube 163.

Hereinafter, referring to FIGS. 6 to 9, the air pumping unit 116 will be described in detail. As described above, the air pumping unit 116 according to the invention is disposed in the main body 10 and is connected to the air-pressure supplier 150 of the wax dispenser 100 via the air cable 15.

The air pumping unit 116 discharges air to the air-pressure supplier 150 via the air cable 15 or sucks in air from the air-pressure supplier 150 such that the air-pressure supplier 150 operates in either a pressurization mode or a depressurization mode. In other words, the discharge of air from the air pumping unit 116 causes the air-pressure supplier 150 to operate in the pressurization mode and the suction of air into the air pumping unit 116 causes the air-pressure supplier 150 to operate in the depressurization mode.

Figure 6:
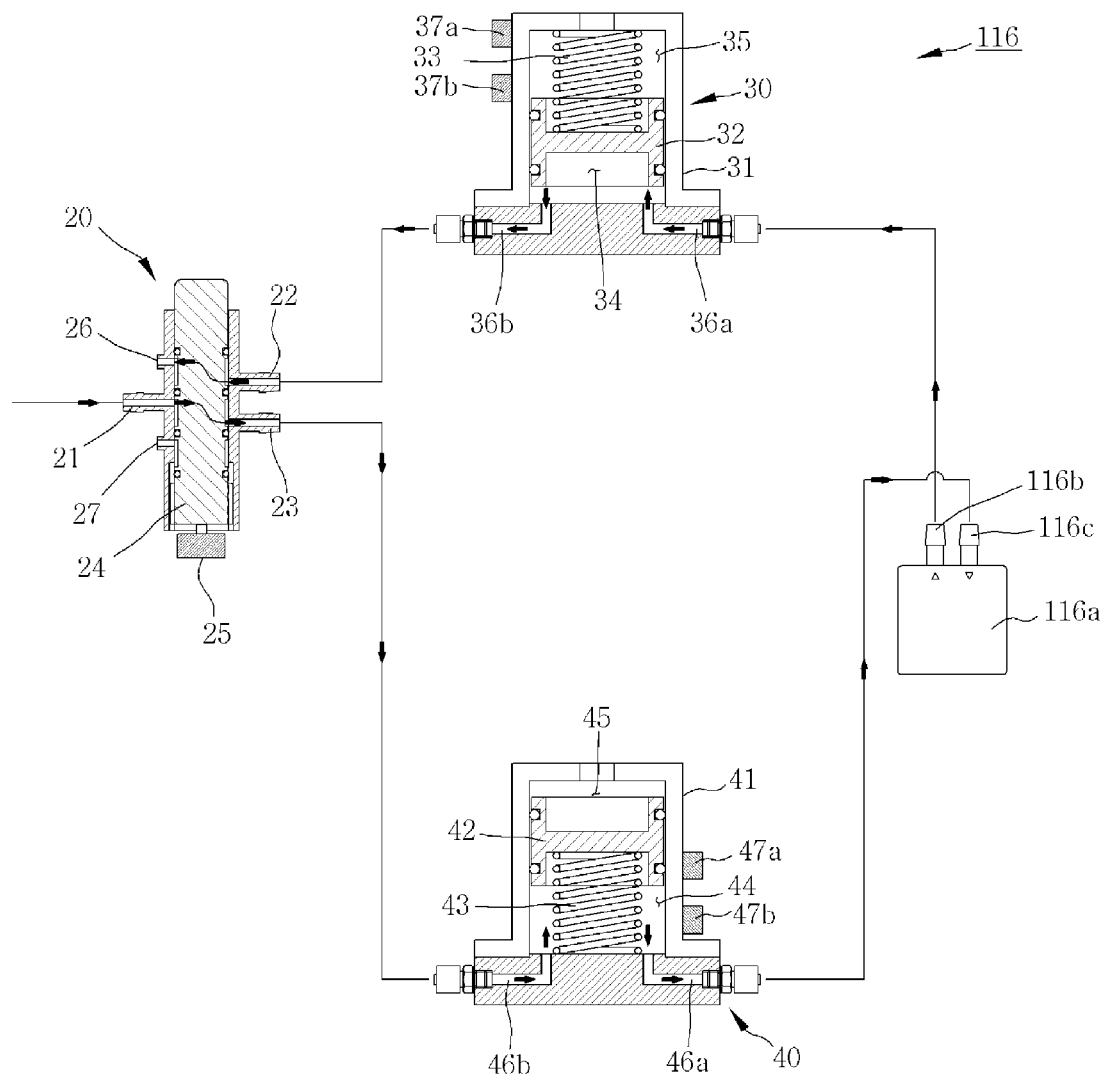
FIGS. 6 and 7 represent one example of the air pumping unit of the wax dispenser system for dental technology according to the first embodiment of the invention.
Figure 7:
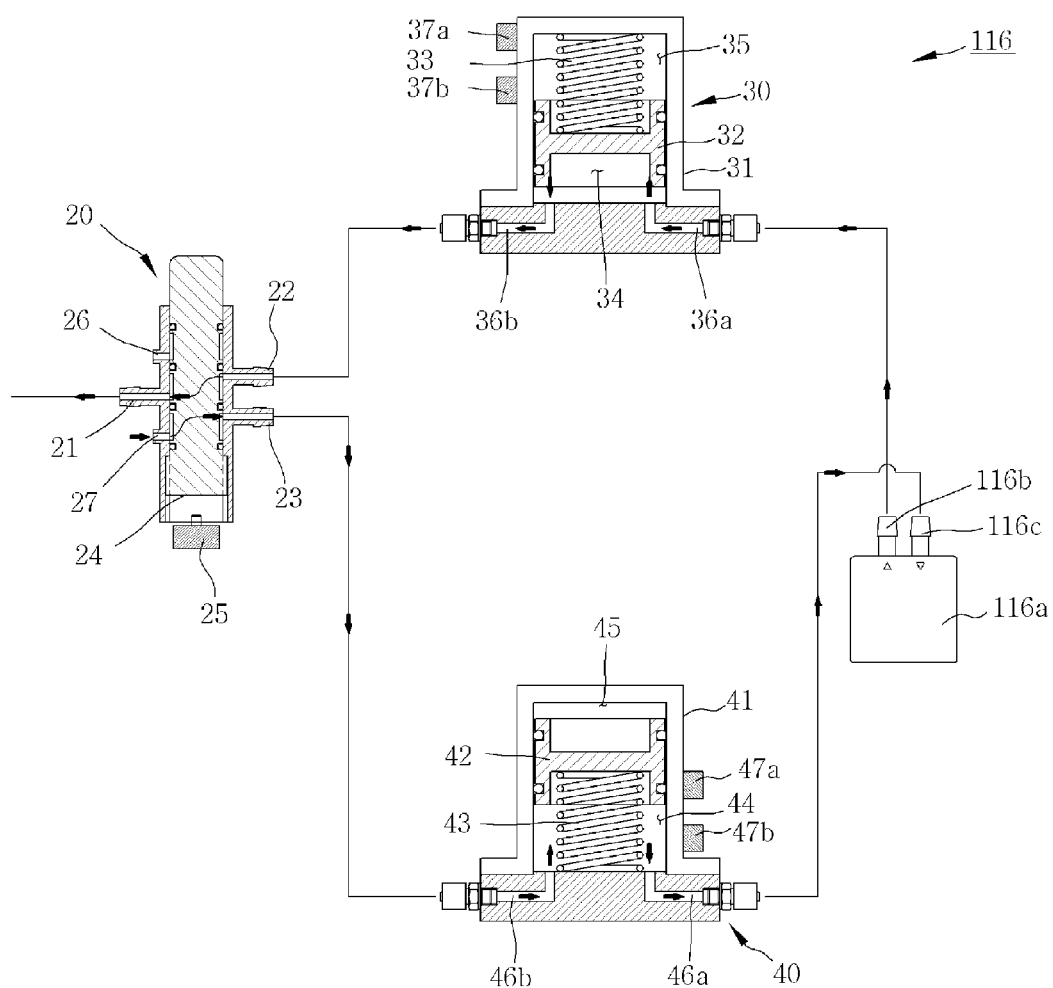

FIGS. 6 and 7 represent one example of the air pumping unit 116 according to the invention. FIG. 6 illustrates a circuit of air in the depressurization mode of the air-pressure supplier 150 and FIG. 7 illustrates a circuit of air in the pressurization mode of the air-pressure supplier 150.

Referring to FIGS. 6 and 7, the air pumping unit 116 according to the invention comprises an air pump 116a and a mode-switching valve 20. Also, the air pumping unit 116 may comprise a discharge air-pressure controller 30 and a suction air-pressure controller 40.

The air pump 116a generates a compressed air to discharge air, or it sucks air as an air-suction pump. Here, the air pump 116a comprises a pumping discharge port 116b for the discharge of air and a pumping suction port 116c for the suction of air.

The mode-switching valve 20 connects selectively one of the pumping discharge port 116b and the pumping suction port 116c to the air cable 15. That is, when the mode-switching valve 20 connects the pumping discharge port 116b of the air pump 116a to the air cable 15, the air-pressure supplier 150 operates in the pressurization mode. Contrary to this, when the mode-switching valve 20 connects the pumping suction port 116c of the air pump 116a to the air cable 15, the air-pressure supplier 150 operates in the depressurization mode.

As shown in FIGS. 6 and 7, the mode-switching valve 20 comprises a cable connection port 21, a discharge connection port 22, a suction connection port 23 and a valve switch 24. Also, the mode-switching valve 20 comprises a first dummy port 27 and a second dummy port 26. In one example, the mode-switching valve 20 is embodied in the form of a 5-port switching valve.

The cable connection port 21 is connected to the air cable 15, the discharge connection port 22 is connected to the pumping discharge port 116b, and the suction connection port 23 is connected to the pumping suction port 116c. The first dummy port 27 and the second dummy port 26 are opened to the outside, respectively and independently.

Here, the valve switch 24 is operated either in the first switching position in which the cable connection port 21 is connected to the discharge connection port 22 or in the second switching position in which the cable connection port 21 is connected to the suction connection port 23. If the valve switch is in the first switching position in which the cable connection port 21 is connected to the discharge connection port 22, the air-pressure supplier 150 operates in the pressurization mode, and if the valve switch is in the second switching position in which the cable connection port 21 is connected to the suction connection port 23, the air-pressure supplier 150 operates in the depressurization mode. In one example, the valve switch 24 is manipulated by the manual operation of the lever 25, but an electronically-driven valve such as a solenoid valve may be used.

The valve switch 24 in the first switching position causes the suction connection port 23 to be connected to the first dummy port 27, and then the suction force through the pumping suction port 116c of the air pump 116a during the pressurization mode is transferred to the first dummy port 27, so that outside air is introduced through the first dummy port 27.

On the other hand, the valve switch 24 in second first switching position causes the discharge connection port 22 to be connected to the second dummy port 26, and then air which is discharged through the pumping discharge port 116b of the air pump 116a during the depressurization mode is discharged to the outside through the second dummy port 26.

The discharge air-pressure controller 30 is disposed on an air line which connects the pumping discharge port 116b to the discharge connection port 22 so as to control the pressure of air which is discharged from the pumping discharge port 116b of the air pump 116a. The suction air-pressure controller 40 is disposed on an air line which connects the pumping suction port 116c to the suction connection port 23 so as to control the pressure of air which is introduced into the air pump 116a.

The discharge air-pressure controller 30 and the suction air-pressure controller 40 are embodied as an air pressure cylinder which temporarily contains air discharged from the air pump 116a or air introduced into the air pump 116a and then discharges or sucks the air at a predetermined air pressure.

Referring to FIGS. 6 and 7, the discharge air-pressure controller 30 comprises a first cylinder 31, a first piston 32 and a first spring member 33.

The first cylinder 31 forms a receiving section in which the first piston 32 is able to move back and forth. The first piston 32 is adapted to move back and forth in the first cylinder 31 and the first piston 32 divides the inner section of the first cylinder 31 into a first section 34 and a second section 35.

The first spring member 33 of the discharge air-pressure controller 30 is received in the second section 35 of the first cylinder 31 to provide the first piston 32 with a spring force toward the first section 34. The first section 34 of the cylinder 31 forms an air passage between the pumping discharge port 116b and the discharge connection port 22.

According to the above arrangement, if the air pump 116a begins to work while air flow to the discharge connection port 22 is being blocked (e.g., when the side button 164 is not working), air discharged through the pumping discharge port 116b of the air pump 116a is introduced into the first section 34 of the first cylinder, which causes the increase of air pressure and then the movement of the first piston 32 toward the second section 35.

After the first piston 32 is moved to the second section 35, if air flows to the discharge connection port 22 and then the air pump 116a is stopped, the first spring member 33 moves the first piston 32 back to the first section 34 and then air pressure generated by the movement of the first piston 32 causes air to flow toward the discharge connection port 22.

In accordance with the arrangement as described above, it is possible to control the quantity of air discharged from the air pumping unit 116 and air pressure thereof by adjusting the size of the first cylinder 31 and the spring force of the first spring member 33.

The discharge air-pressure controller 30 comprises a first position sensor 37a, 37b which detects the position of the first piston 32. When the first piston 32 is displaced toward the first spring member 33 by a predetermined distance, the first position sensor 37a, 37b detects the displacement to stop the operation of the air pump 116a. On the contrary, when the first piston 32 is displaced in the opposite direction by a spring force of the first spring member 33, the first position sensor 37a, 37b detects the displacement to restart the air pump 116a. In one example, the first position sensor 37a, 37b is provided in the form of a magnetic sensor and a pair of the first position sensors are provided along the moving direction of the first piston 32 to detect the top dead center and the bottom dead center of the first piston 32.

Similarly, the suction air-pressure controller 40 comprises a second cylinder 41, a second piston 42 and a second spring member 43.

The second cylinder 41 forms a receiving section in which the second piston 42 is able to move back and forth. The second piston 42 is adapted to move back and forth in the second cylinder 41 and the second piston 42 divides the inner section of the second cylinder 41 into a third section 44 and a fourth section 45.

The second spring member 43 of the suction air-pressure controller 40 is received in the third section 44 of the second cylinder 41 to provide the second piston 42 with a spring force toward the fourth section 45. The third section 44 of the second cylinder 41 forms an air passage between the pumping suction port 116c and the suction connection port 23.

According to the above arrangement, if the air pump 116a begins to work while air flow from the suction connection port 23 is being blocked (e.g., when the side button 164 is not working), air is introduced through the pumping suction port 116c of the air pump 116a, which causes the decrease of air pressure in the third section 44 of the second cylinder 41 and then the movement of the second piston 42 toward the third section 44.

After the second piston 42 is moved to the third section 44, if air flows from the suction connection port 23 and then the air pump 116a is stopped, the second spring member 43 moves the second piston 42 back to the fourth section 45 and then air pressure generated by the movement of the second piston 42 causes air to be introduced from the suction connection port 23.

In accordance with the arrangement as described above, it is possible to control the volume of air introduced into the air pumping unit 116 and air pressure thereof by adjusting the size of the second cylinder 41 and the spring force of the second spring member 43.

The suction air-pressure controller 40 comprises a second position sensor 47a, 47b which detects the position of the second piston 42. When the second piston 42 is displaced toward the third section 44 by a predetermined distance, the second position sensor 47a, 47b detects the displacement to stop the operation of the air pump 116a. On the contrary, when the second piston 42 is displaced in the opposite direction by a spring force of the second spring member 43, the second position sensor 47a, 47b detects the displacement to restart the air pump 116a. In one example, the second position sensor 47a, 47b is provided in the form of a magnetic sensor and a pair of the second position sensors are provided along the moving direction of the second piston 42 to detect the top dead center and the bottom dead center of the second piston 42.

Further, reference numerals 36a, 36b, 46a and 46b, respectively in FIGS. 6 and 7 indicate an inlet/outlet port provided at the discharge air-pressure controller 30 and the suction air-pressure controller 40.

Figure 9:
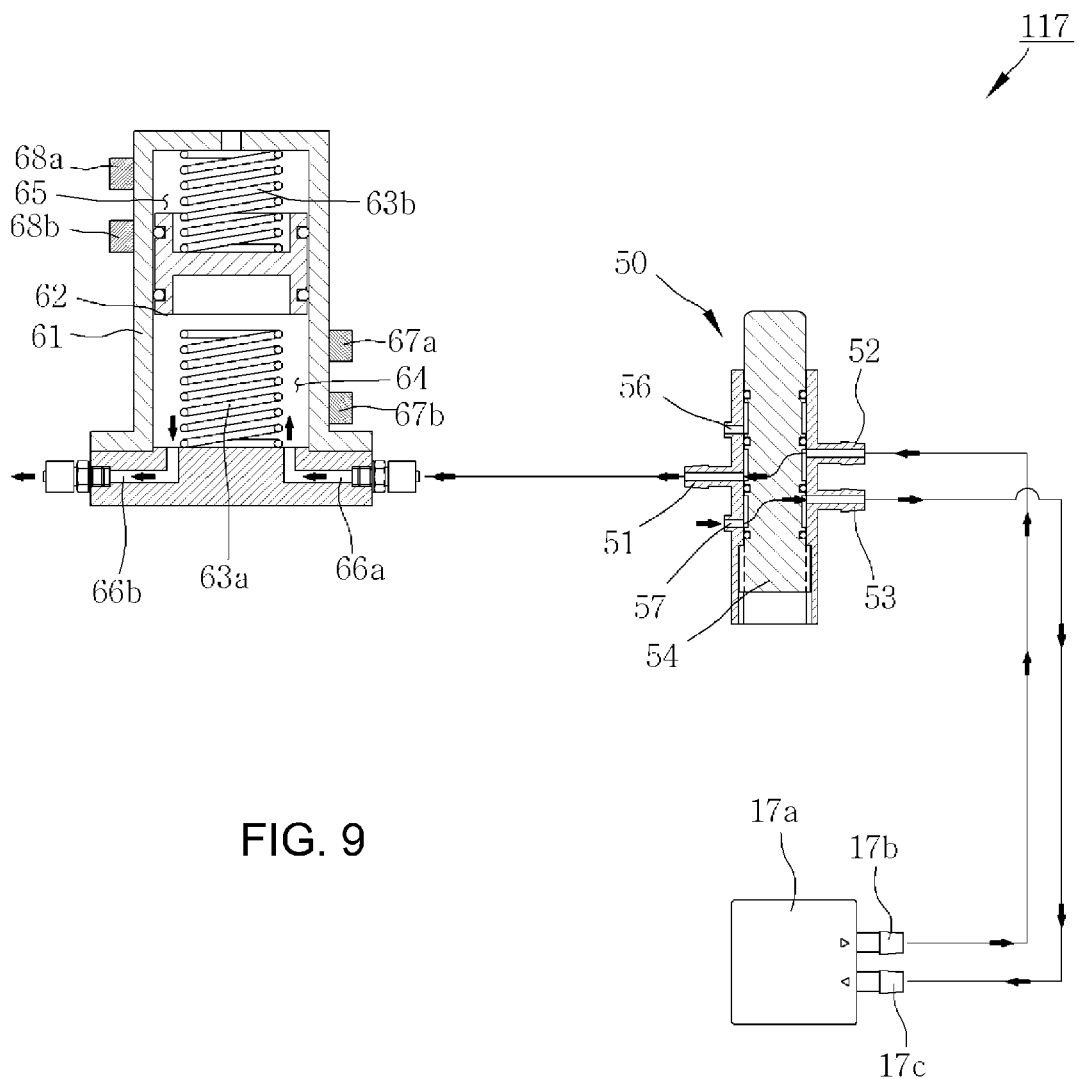

FIGS. 8 and 9 represent another example of air pumping unit 117. FIG. 8 shows an air flow when the air-pressure supplier 150 is operated in the depressurization mode and FIG. 9 shows an air flow when the air-pressure supplier 150 is operated in the pressurization mode. FIGS. 8 and 9 are the modifications of the embodiments of FIGS. 6 and 7 and hereinafter, the difference will be described.

A pumping discharge port 117b of an air pump 117a is directly connected to a discharge connection port 52 of a mode switching valve 50, and a pumping suction port 117c of an air pump 117a is directly connected to a suction connection port 53 of a mode switching valve 50. A combined air-pressure controller 60 is disposed on the air line which connects a cable connection port 51 of the mode switching valve 50 to the air cable 15. The mode switching valve 50 is provided with a pair of dummy ports 56, 57.

The combined air-pressure controller 60 is arranged to control the air-pressure of air discharged from the air pump 117a and to control air-pressure of air introduced to the air pump 117a.

Referring to FIGS. 8 and 9, the combined air-pressure controller 60 comprises a combined cylinder 61, a combined piston 62, a discharge spring member 63b and a suction spring member 63a. The combined cylinder 61 is divided into a fifth section 64 and a sixth section 65 by means of a combined piston 62. The discharge spring member 63b is received in the sixth section 65 and exerts spring force to the combined piston 62 toward the fifth section 64 and the suction spring member 63a is received in the fifth section 64 and exerts spring force to the combined piston 62 toward the sixth section 65.

According to the above arrangement, if air from the air pump 117a is introduced to the combined air-pressure controller 60, the operation of the discharge spring member 63b and the combined piston 62 causes the air-pressure controller 60 to act as the discharge air-pressure controller 30 as described above. Also, if the suction from the air pump 117a is provided to the combined air-pressure controller 60, the operation of the suction spring member 63a and the combined piston 62 causes the combined air-pressure controller 60 to act as the suction air-pressure controller 40 as described above.

Reference numerals 66a and 66b in FIGS. 8 and 9 indicate inlet/outlet port in the combined air-pressure controller 60, and reference numerals 67a, 67b, 68a and 68b indicate position sensors in the combined piston 62 which correspond to the first position sensor 37a, 37b of the discharge air-pressure controller 30 and the second position sensor 47a, 47b of the suction air-pressure controller 40.

Figure 10:
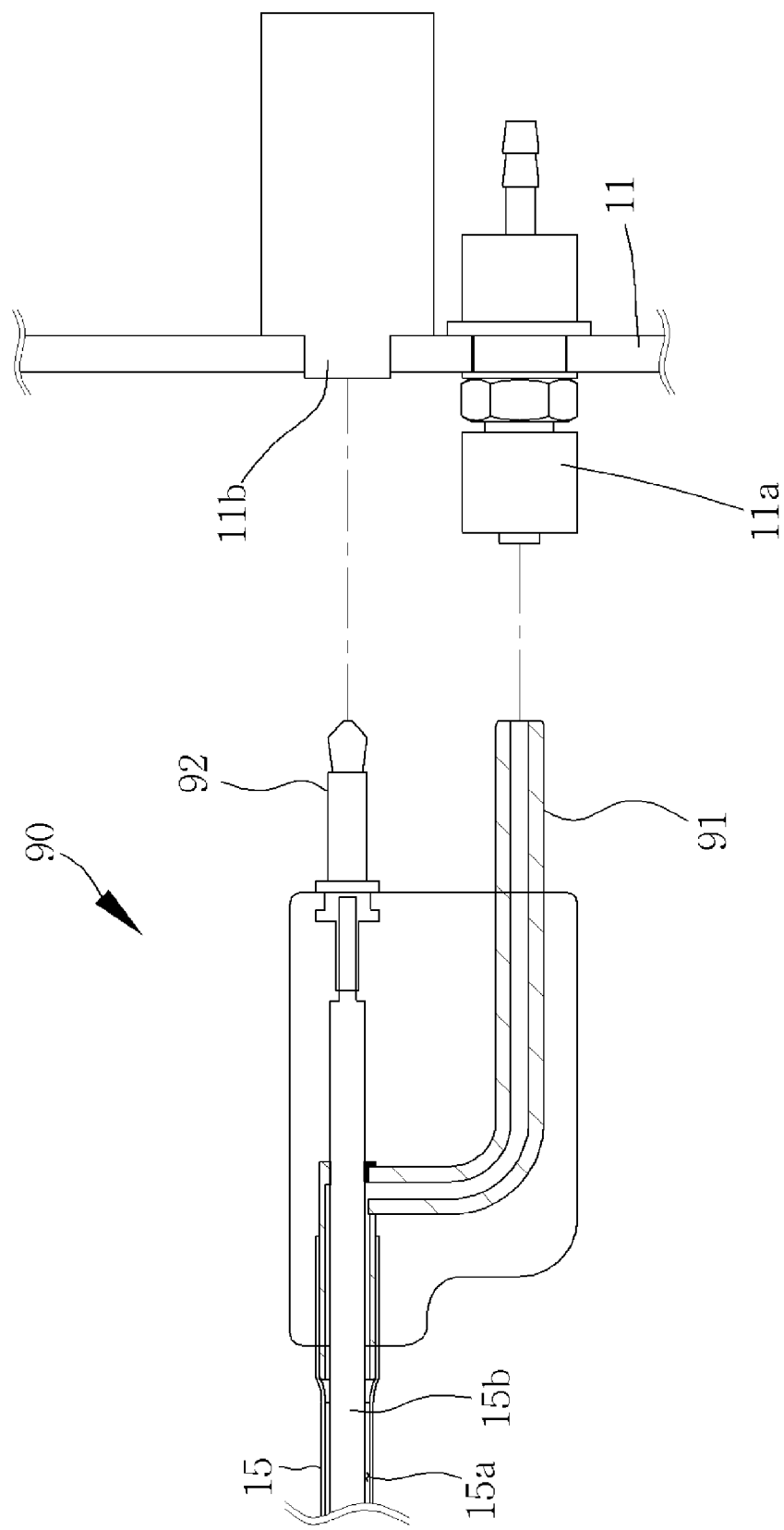
FIG. 10 represents a sectional view of a connection module of the wax dispenser system for dental technology according to the first embodiment of the invention.

The heater 140 according to the invention receives power from the power supply (not shown) in the main body 10 for heat dissipation of the heating member 142. The power supply (not shown) is electrically connected to the heater 140 by the power cable 15b. In one example, as shown in FIG. 10, the power cable 15b extends in the air cable 15 to be connected to the heater 140. Air flows in the gap 15a between the inner surface of the air cable 15 and the power cable 15b.

As shown in FIG. 10, the body case which constitutes an outer part of the main body 10 comprises an air connection port 11a which is connected to the air pumping unit 116 and a power connection port 11b which is connected to the power supply.

The edge of the air cable 15 is provided with a connection module 90 for the connection to the air connection port 11a and the power connection port 11b. The connection module 90, as shown in FIG. 10, is electrically connected to the power cable 15b disposed in the air cable 15 and comprises a power connection jack 92 which is connectable to the power connection port 11b and an air connection jack 91 which is in fluid communication with the air cable 15 and which is connectable to the air connection port 11a.

Accordingly, as shown in FIGS. 1 and 10, only the connection of the connection module 90 installed at the air cable 15 to the main body 10 will result in the electrical connection of the wax dispenser 100 to the main body 10 as well as the connection of air line.

As shown in FIG. 1, the main body 10 is provided with the controller 13 and the wax tank 12. The controller 13 is able to control the temperature of the heater 140, the mode switching valve 20, etc. according to the user's setting.

Second Exemplary Embodiment

Figure 11:
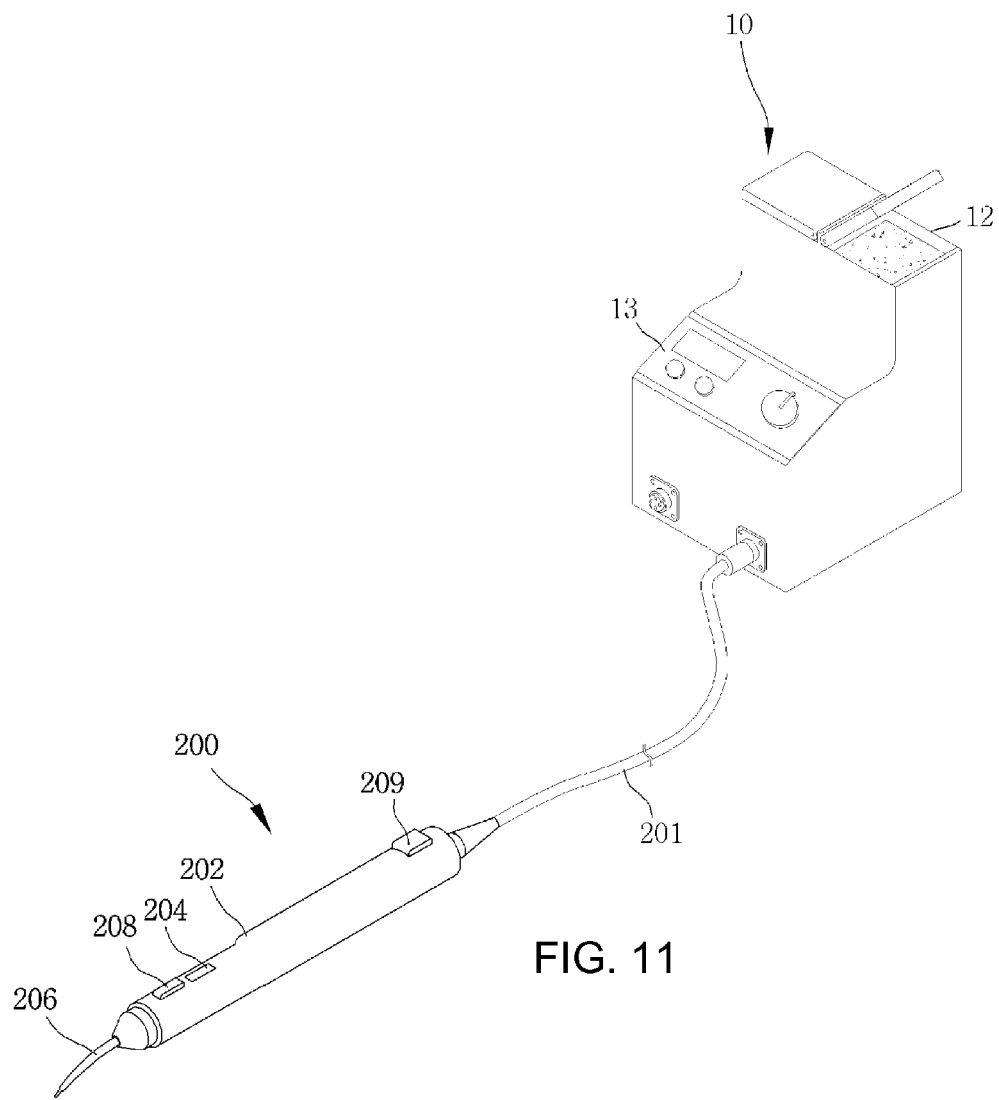
FIG. 11 represents a wax dispenser system surrounding to which a wax dispenser system for dental technology according to a second embodiment of the invention is applied.

FIG. 11 represents a wax dispenser system surrounding to which a wax dispenser system for dental technology according to the invention is applied.

As shown in FIG. 11, the wax dispenser system for dental technology comprises a wax dispenser 200 and a main body 10 which is used for the dispenser.

The wax dispenser 200 comprises constitutional elements in a housing 202 which is in the shape of a pen. The housing 202 has a reservoir which charges and stores wax and a heater therein. The housing 202 has, on its outer surface, a window 204 by which the quantity of wax is observed and a side button 208 which controls the quantity of wax to be discharged through a nozzle 206. As will be described below, the outer part of the housing 202 is provided with a further side button 209 which adjusts the rotation direction of the motor installed inside the wax dispenser 200. As such, the wax dispenser 200 is in the shape of a pen and thus a user is able to grip and operate the dispenser easily during the work of false teeth.

The main body 10 comprises a wax tank 12 and a controller 13. The wax tank 12 receives a wax in a solid state and then wax is heated by means of a heater installed therein to become in a liquid wax. When wax is melted to be a liquid wax, a user manipulates the side button 209 of the wax dispenser 200 to set the rotation direction of a motor in the wax dispenser 200 to the opposite direction and then pushes the side button 208 to actuate the motor.

Then, it is possible to fill wax in the wax dispenser 200 by the suction of a liquid wax contained in the wax tank 12. The controller 13 controls the temperature of the wax tank 12 according to the user's settings and supplies power to the wax dispenser 200 via the power cable 201. Also, the controller 13 is able to control the temperature of the heater disposed in the wax dispenser 200.

Figure 12:
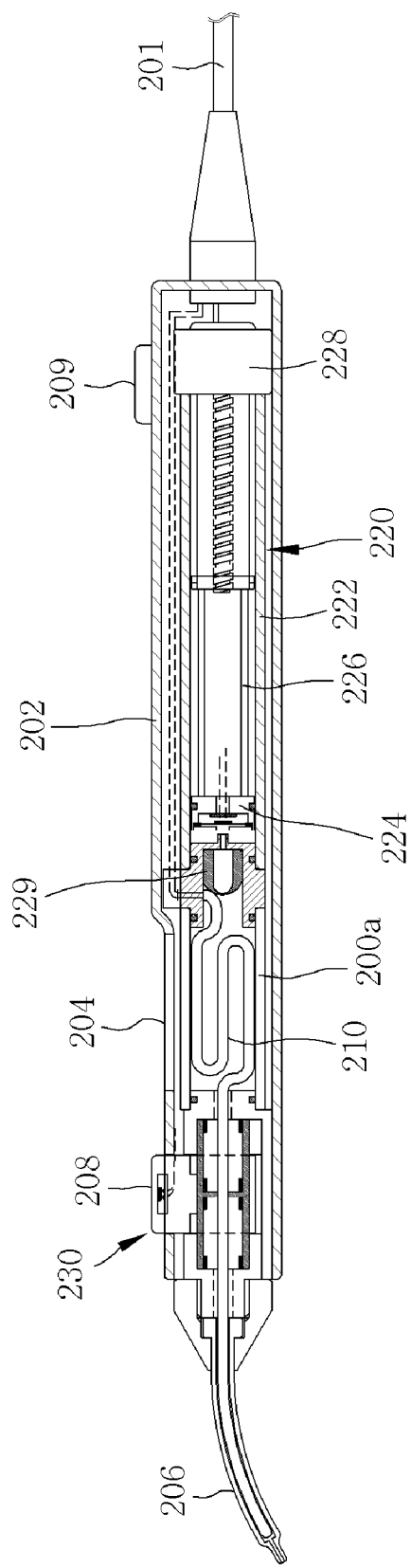
FIG. 12 represents a sectional view of a wax dispenser system for dental technology according to a second embodiment of the invention.

FIG. 12 represents a sectional view of a wax dispenser system for dental technology according to another embodiment of the invention.

As shown in FIG. 12, the wax dispenser 200 comprises a wax reservoir 200a, a nozzle 206, a heater 210 and a cylinder 220.

The wax reservoir 200a is in the shape of a hollow tube having transparent material and contains a liquid wax therein. For example, the wax reservoir 200a is made of glass. As such, the transparent wax reservoir 200a allows user to check the quantity of filled wax through the window 204 of the housing 202. In one example, a scale is marked on the window 204 or the wax reservoir 200a to check the quantity of filled wax quantitatively.

The nozzle 206 is in the shape of a fine hollow tube and is disposed in the front end of the reservoir 200a to discharge wax contained in the wax reservoir 200a. In one example, the nozzle 206 is configured to be detachable in such a manner that the nozzle can be replaced with another nozzle having an appropriate size and bore according to the required work.

The heater 210 maintains wax contained in the wax reservoir 200a and wax discharged through the nozzle 206 in a liquid state by means of a wire-shaped heating member which is disposed in the wax reservoir 200a and one end of which is inserted into the hollow part of the nozzle 206. As such, the heating member of the heater 210 is disposed in the wax reservoir 200a and is inserted into the hollow port of the nozzle 206, thereby the solidification of wax which may occur near the discharging outlet of the nozzle during the work is prevented and also it is possible to heat wax properly in a degree not to spoil wax in order to maintain the temperature of the wax reservoir 200a and the nozzle 206 to a predetermined value.

The cylinder 220 discharges wax contained in the wax reservoir 200a through the nozzle 206 by applying air pressure to the inner space of the wax reservoir 200a at the rear part of the wax reservoir 200a, or introduces wax into the wax reservoir 200a through the nozzle 206 by suction.

For this, the cylinder 220 comprises a cylinder tube 222, a piston unit 224 and 226 and a motor driving device 228. The cylinder tube 222 is connected to the rear part of the wax reservoir 200a. The piston unit 224 and 226 moves in a straight line in the cylinder tube 222 to apply air pressure to the inner space of the wax reservoir 200a. The motor driving device 228 moves the piston unit 224 and 226 in a straight line by the rotational force of a motor. Here, the motor driving device 228 rotates a screw having thread and the piston unit 224 and 226 comprises a hole which has screw fastening with the screw in such a manner that the piston unit 224 and 226 moves forward or backward according to the rotation direction of the screw. For example, the piston unit 224 and 226 comprises a piston head 224 and a piston rod 226. The piston rod 226 has a hole which has screw fastening with the screw to move forward or backward according to the rotation direction of the motor driving device 228. The piston head 224 is engaged with the piston rod 226 to generate air pressure by the forward or backward movement of the piston rod 226.

Figure 13:
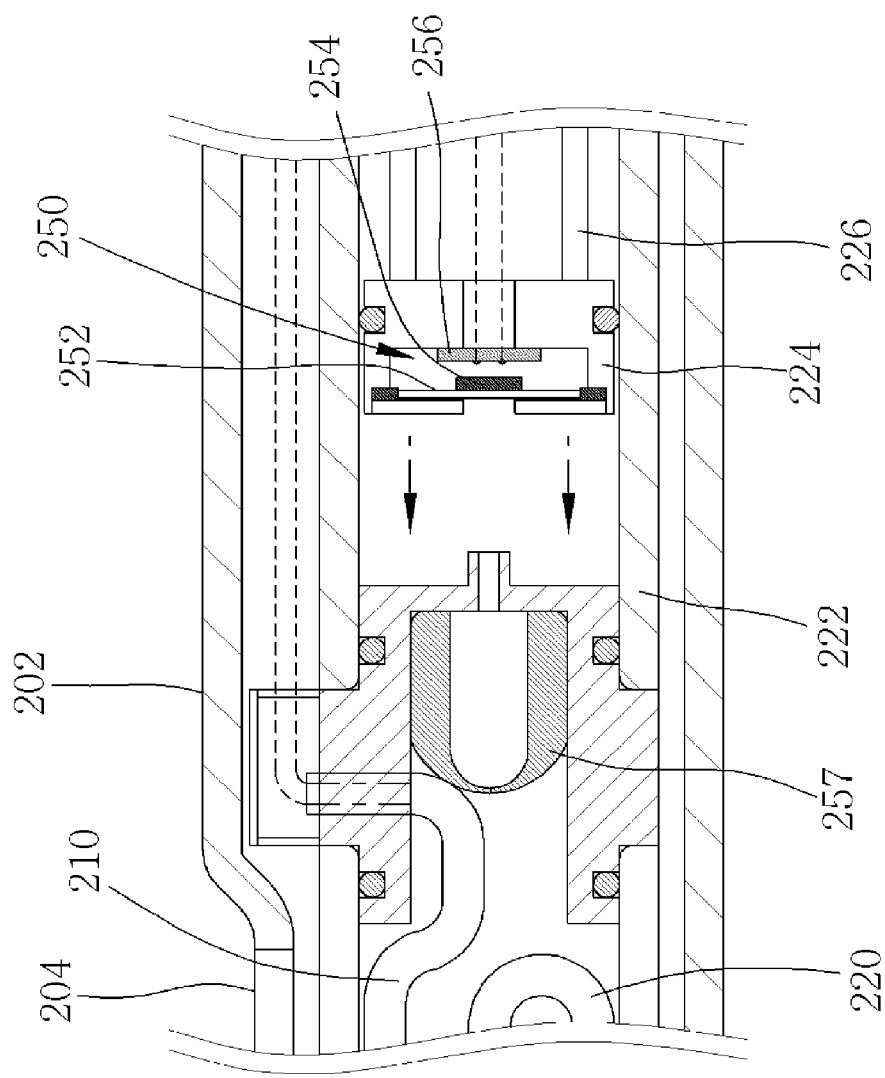
FIGS. 13 and 14 schematically represent a partial sectional view of the operation of the cylinder according to the second embodiment of the invention and FIG. 15 schematically shows a partial sectional view of an example of the discharge controller according to the second embodiment of the invention.
Figure 14:
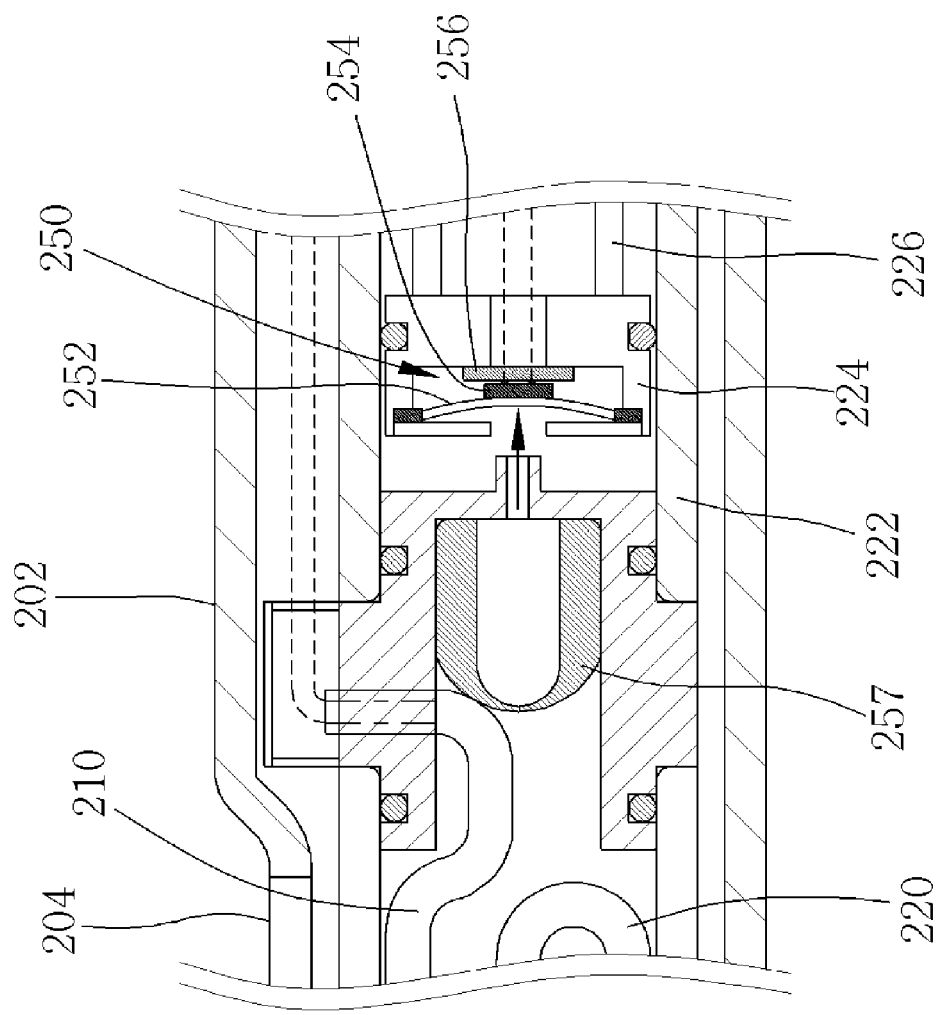

FIGS. 13 and 14 represent a partial sectional view of the operation of the cylinder 220.

As shown in FIGS. 13 and 14, the cylinder 220 further comprises a diaphragm unit 250. The diaphragm unit 250 is disposed in the piston head 224 and stops the motor driving device 228 when the air pressure in the wax reservoir 200a reaches a predetermined critical value. For this, the diaphragm unit 250 comprises a diaphragm 252 which is an elastic membrane made of metal or nonmetal and which transforms air pressure into displacement and stop switches 254 and 256 which stops the operation of the motor driving device 228 according to the position of the diaphragm 252. First, as shown in FIG. 13, if the operation of the motor driving device 228 causes the piston unit 224 and 226 to move forward, the inner pressure of the wax reservoir 200a and the cylinder tube 222 increases. Therefore, as shown in FIG. 14, the diaphragm 252 is pushed into the piston head 224, which causes a short circuit of the stop switches 254 and 256 and thus blocks the power supplied to the motor driving device 228. As configured above, the quantity of wax discharged by excessive air pressure in the wax dispenser 200 is prevented from being increased more than necessary and it is possible to control the quantity of discharged wax precisely.

Meanwhile, the cylinder 220 may further comprise a backflow preventer cap 257. The backflow preventer cap 257 transfers air pressure generated by the straight movement of the piston unit 224 and 226 to the inner space of the wax reservoir 200a through a micro-hole and prevents the backflow of wax contained in the wax reservoir 200a. As configured above, the leakage of wax is prevented regardless of how the wax dispenser 200 is positioned.

Meanwhile, the wax dispenser 200 may further comprise a discharge controller 230. The discharge controller 230 allows a wax passage 278 to be provided between the wax reservoir 200a and the nozzle 206, and controls the quantity of discharged wax by opening and closing the wax passage 278.

Figure 15:
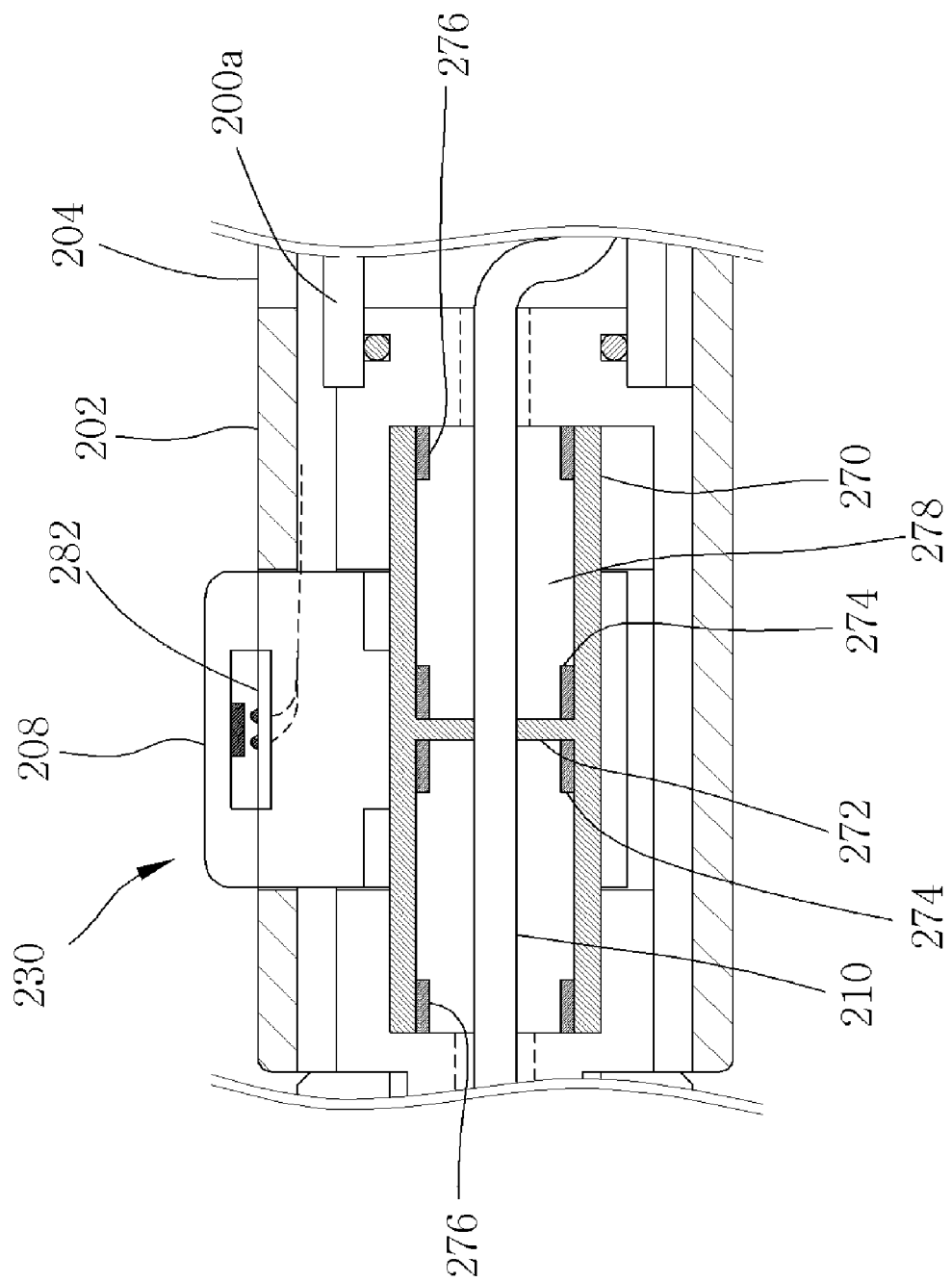

FIG. 15 shows a partial sectional view of an example of the discharge controller 230.

As shown in FIG. 15, the discharge controller 230 may comprise an elastic tube 270 and a side button 208. The elastic tube 270 which is a hollow tube made of an elastic material constitutes at least a portion of the wax passage 278 and is configured such that one part of the inner surface 272 is in close contact with the outer surface of the heating member 210 which penetrates through the wax passage 278 and which is inserted into the nozzle 206. The side button 208 is disposed on the outer surface of the elastic tube 270 and is configured such that the push of the side button 208 causes power to be supplied to the motor driving device 228 and causes the elastic tube 270 to be pressed and deformed to separate the inner surface 272 of the elastic tube 270 from the heating member 210. For this, the side button 208 is made of an elastic material having a hollow part 280 and is disposed on the top of the elastic tube 270 in a radial direction. Also, the hollow part 280 of the side button 208 is provided with an actuation switch 282 and the switch 282 is configured such that the push of the side button 208 causes a short-circuit of the switch and then power is supplied to the motor driving device 228. The inner part of the elastic tube 270 is provided with a metal ring 274 which supports the elastic tube 270 and a sealing ring 276 which prevents a leakage of wax which flows through the elastics tube 270. As such, the discharge controller 230 will allow user to control the quantity of wax discharged from the wax dispenser 200 more precisely by simply pushing the button with a finger during the work.

As explained above, according to the invention, it is possible to facilitate user's convenience and the work efficiency by using wax charged in the wax dispenser having an embedded heater in the shape of a pen, by discharging wax with air pressure and by controlling the discharge of wax precisely. Also, it is possible to prevent the blockage of the nozzle due to the solidification of wax or the alteration of wax due to the overheating during the work by making wax discharged through the nozzle heated to proper temperature. Further, it is possible to prevent charged wax from leaking regardless of how the wax dispenser is positioned, thereby the safety being ensured and user's convenience being improved. Moreover, the embodiments of the invention may solve other technical problems including those described above in the field of the invention as well as other fields relating to the invention.

Third Exemplary Embodiment

Figure 16:
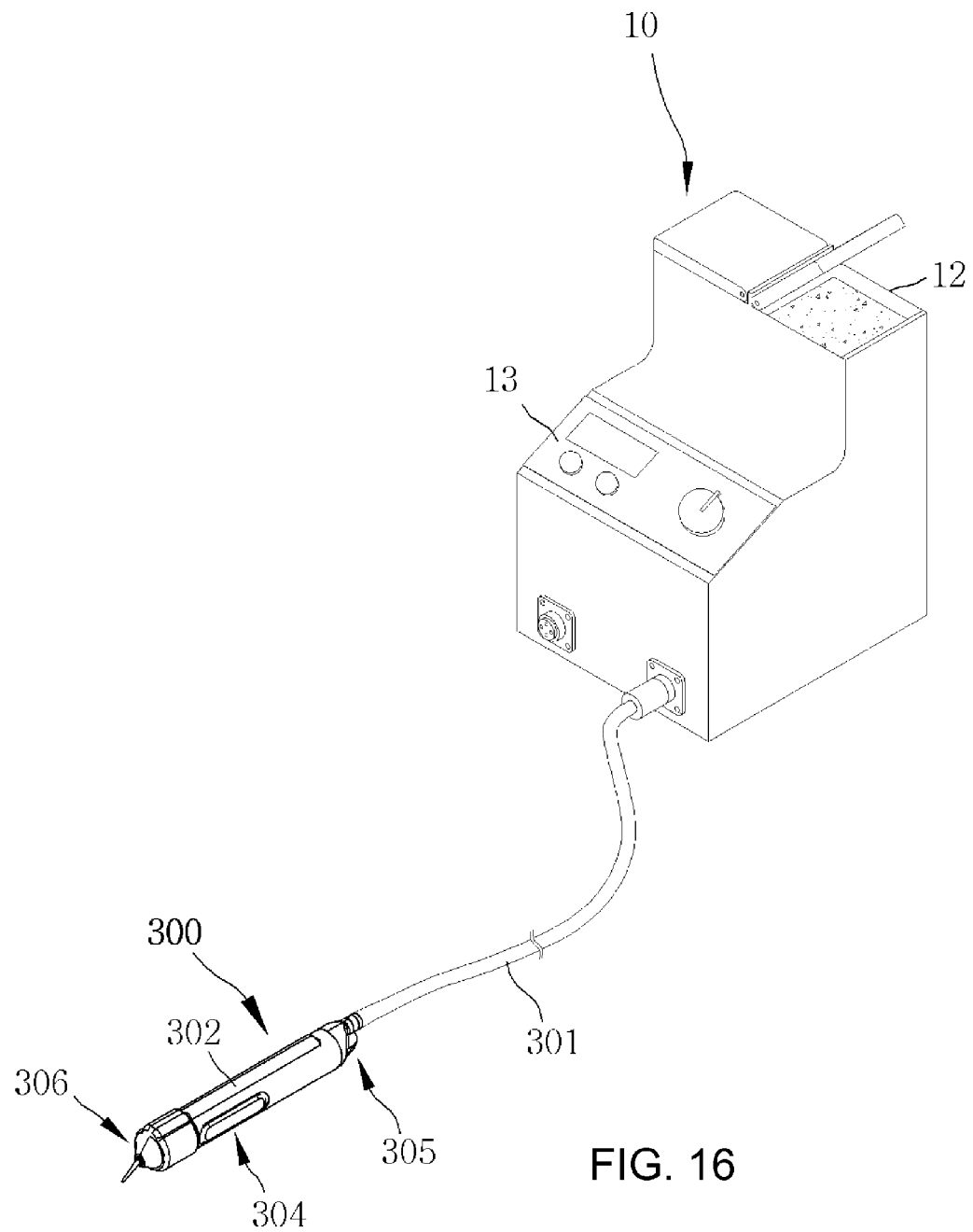
FIG. 16 schematically represents a wax dispenser system surrounding to which a wax dispenser system for dental technology according to a third embodiment of the invention is applied.

FIG. 16 represents a wax dispenser system surrounding to which a wax dispenser system for dental technology according to the third embodiment of the invention is applied.

As shown in FIG. 16, the wax dispenser system for dental technology comprises a wax dispenser 300 and a main body 10 which is used for the dispenser.

The wax dispenser 300 comprises constitutional elements in a housing 302 which is in the shape of a pen. The housing 302 has a reservoir which charges and stores wax and a heater therein. The housing 302 has, on its outer surface, a press button unit 304 which controls a quantity of wax discharged through a nozzle 306. Also, the housing 302 comprises, on its rear end, a charge button 308 which introduces a liquid wax into the inner reservoir of the wax dispenser 300 through the nozzle 306 by suction. As will be described below, the charge button 308 allows a liquid wax to be introduced into the elastic tube by suction and the introduction is caused by a negative pressure in the elastic tube generated by the elastic force of the elastic tube. As such, the wax dispenser 300 is in the shape of a pen and thus a user is able to grip and operate the dispenser easily during the work of false teeth.

Meanwhile, the main body 10 comprises a wax tank 12 and a controller 13. The wax tank 12 receives a solid wax and then heat the solid wax by an embedded heater to transform the solid wax into a liquid wax. After the wax was melted into a liquid wax, user pushes the press button unit 304 of the wax dispenser 300 to contract the inner elastic tube in the wax dispenser 300, then immerses the nozzle 306 into the liquid wax contained in the wax tank 12 and pushes the charge button 308 to introduce the liquid wax into the elastic tube by suction.

The controller 13 is adapted to control the temperature of the wax tank 12 according to the user's settings and to supply power to the wax dispenser 300 through the power cable 301. Also, the controller 13 is configured to control the temperature of the heater embedded in the wax dispenser 300.

Figure 17:
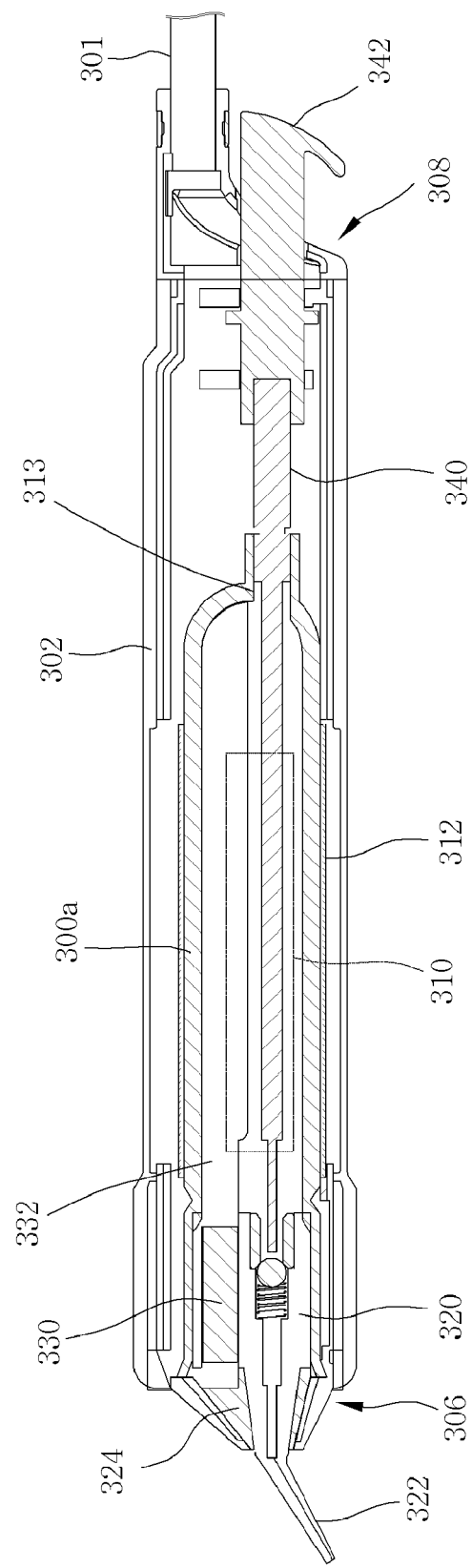
FIG. 17 schematically shows a sectional view of a wax dispenser for dental technology according to the third embodiment of the invention.

FIG. 17 shows a sectional view of a wax dispenser for dental technology according to one example of the invention.

As shown in FIG. 17, the wax dispenser 300 comprises a wax reservoir 300a, a press button unit 304, a nozzle 306, a heater 330 and optionally a charge button 308.

The wax reservoir 300a is a hollow elastic tube and contains a liquid wax therein. For example, the wax reservoir 300a is made of an elastic fire-resistant rubber or other synthetic resins, etc. As such, the wax reservoir 300a is made of an elastic tube such that after the reservoir was deformed due to the external force, it is restored by the elasticity or restoration force when the external force is removed.

The press button unit 304 applies pressure to the wax reservoir 300a when user pushes the button.

Figure 18:
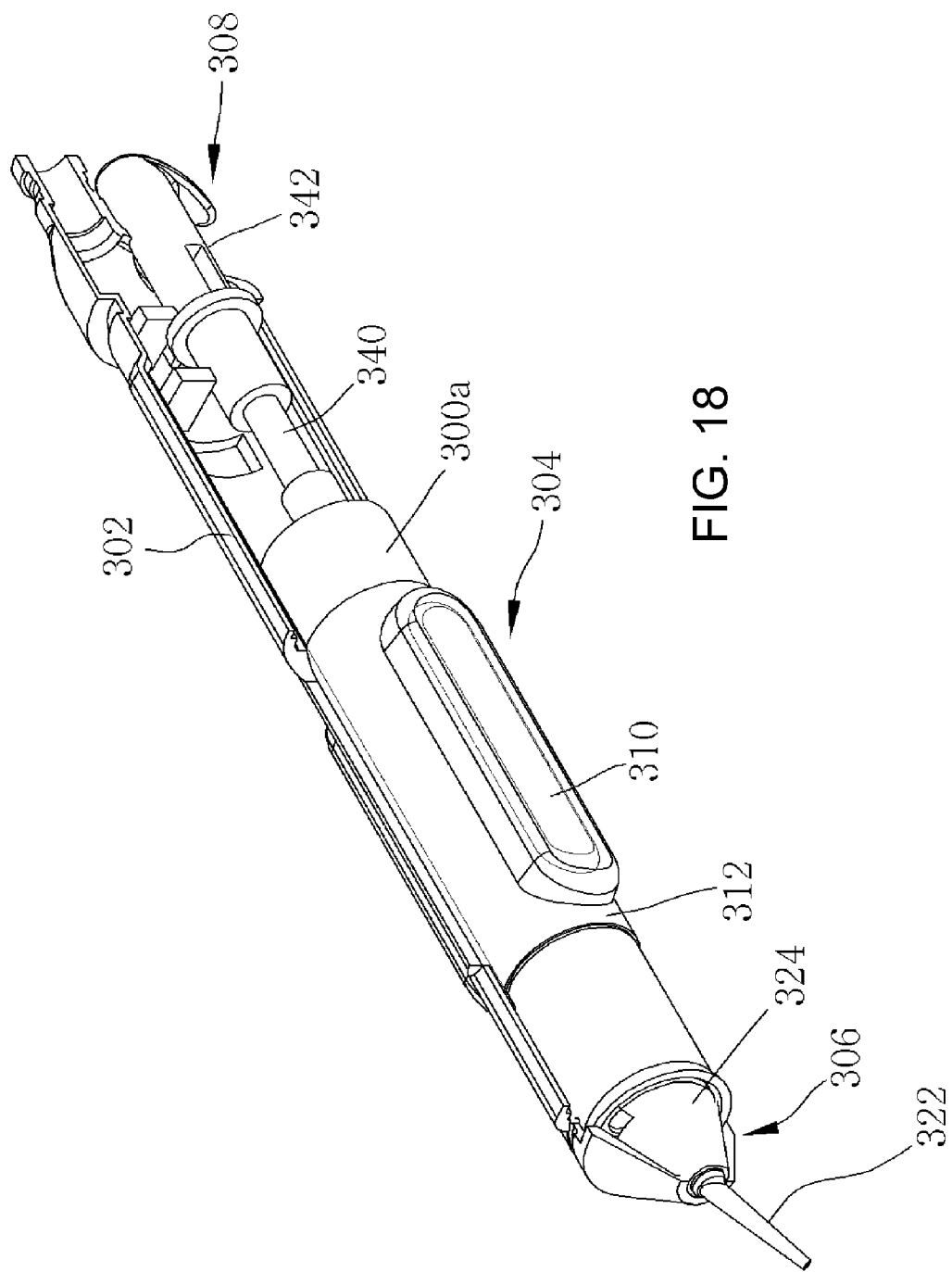
FIG. 18 schematically represents a partial perspective view of the press button unit according to the third embodiment of the invention and FIG. 19 schematically represents a partial sectional view of the nozzle according to the third embodiment of the invention.

FIG. 18 represents a partial perspective view of the press button unit 304.

As shown in FIG. 18, the press button unit 304 comprises a side button 310 and a side button case 312.

The side button 310 is in contact with the outer surface of the wax reservoir 300a and transfers the pressure generated by the push of the button to the wax reservoir 300a. The side button case 312 supports the side button 310 to make the side button 310 contact with the outer surface of the wax reservoir 300a. Since the side button case 312 is made of resilient material such as fire-resistant rubber, it can be deformed and restored by the user's push of the button and heat generated in the wax dispenser 300 can be insulated. The above press button unit 304 allows user to simply push the button with a finger during the work so as to control the quantity of wax discharged from the wax dispenser 300 precisely.

Meanwhile, the nozzle 306 is arranged at the front end of the wax reservoir 300a and discharges wax contained in the wax reservoir 300a when the inner pressure of the wax reservoir 300a is increased by the outer pressure transferred through the press button unit 304 and then exceeds a predetermined critical value.

Figure 19:
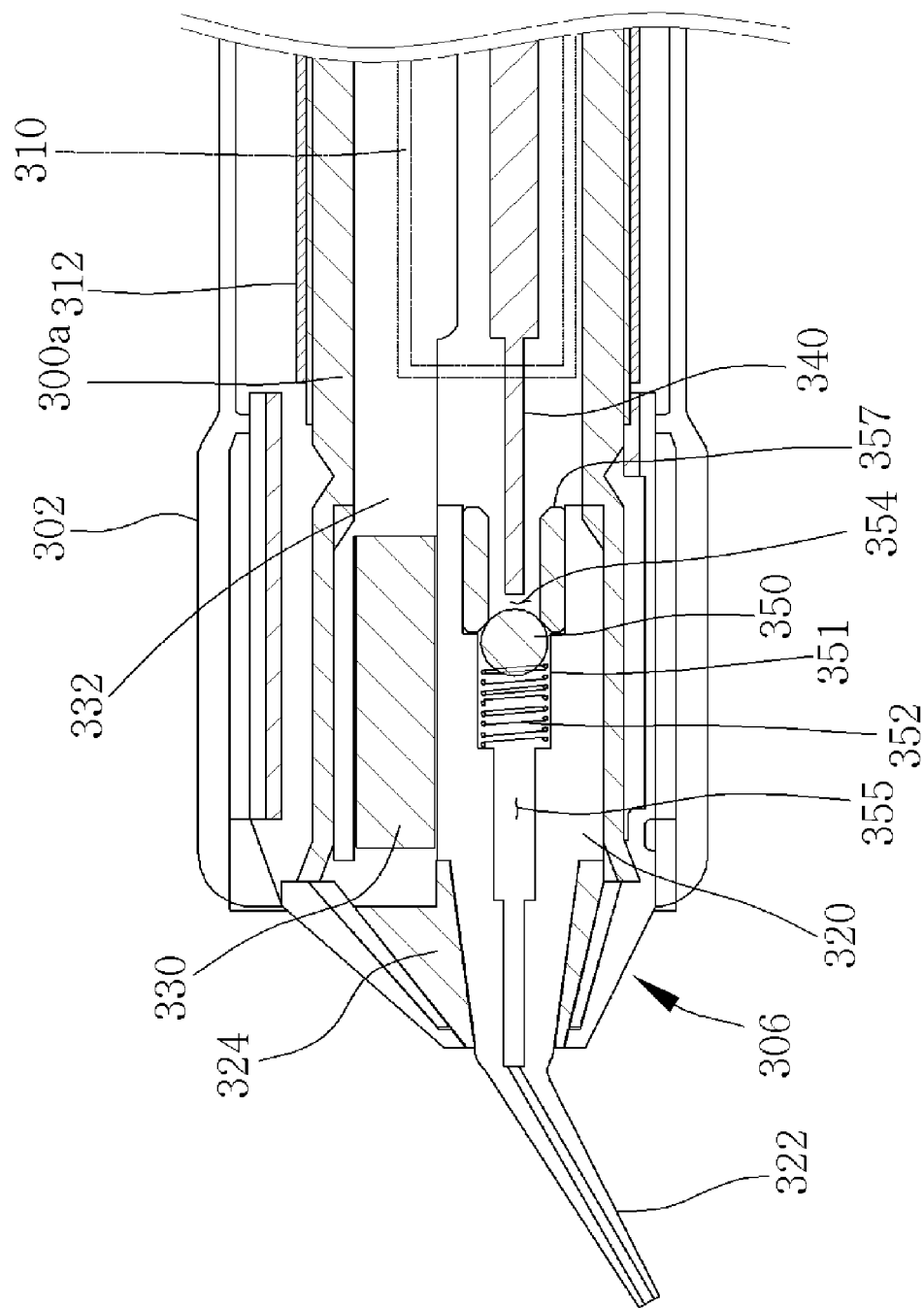

FIG. 19 represents in detail a partial sectional view of the nozzle 306.

As shown in FIG. 19, the nozzle 306 comprises a nozzle valve 320 and a nozzle tube 322.

The nozzle valve 320 blocks wax contained in the wax reservoir 300a when the inner pressure of the wax reservoir 300a is lower than a predetermined critical value, and it allows wax contained in the wax reservoir 300a to pass when the inner pressure of the wax reservoir 300a is greater than a predetermined critical value. For this, the nozzle valve 320 comprises a wax blocking ball 350, a valve tube 351 and a spring member 352. The wax blocking ball 350 is in the shape of a ball and the valve tube 351 contains the wax blocking ball 350 therein. One end of the valve tube 351 is provided with an inlet 354 into which wax contained in the wax reservoir 300a is introduced and the other end of the valve tube 351 is provided with an outlet 355 which discharges wax to the nozzle tube 322. The spring member 352 is configured in the form of a coil spring and presses the wax blocking ball 350 against the inlet 354 in the valve tube 351 to block the inlet 354. In this case, the inner bore of the valve tube 351 is greater than the diameter of the wax blocking ball 350 such that the wax blocking ball 350 is able to move. Alternatively, the inner bore of the inlet 354 is less than the diameter of the wax blocking ball 350 so that the inlet 354 is blocked by the wax blocking ball 350, or the inlet 354 is provided with a bushing 357 having the inner bore smaller than the diameter of the wax blocking ball 350. In this case, the inlet 354 or the bushing 357 may be tapered such that the wax blocking ball 350 becomes in close contact with the inlet or the bushing easily. The nozzle tube 322 is in the shape of a thin hollow tube and discharges wax contained in the wax reservoir 300a to the outside after the wax passes through the nozzle valve 320.

The heater 330 transfers heat to a heat conductor 332 and the nozzle 306 disposed in the wax reservoir 300a so that wax which is contained the wax reservoir 300a and wax which is discharged through the nozzle 306 are kept in liquid state. In this case, the nozzle 306 is made of heat-conductive material and is in contact with the heater 330. Also, the wax dispenser 300 further comprises a nozzle guide tube 324 made of insulating material. The nozzle guide tube 324 is arranged to support the nozzle 306 in the housing 302 of the wax dispenser 300 and prevents heat loss, i.e., prevents heat transferred from the heater 330 to the nozzle 306 from transferring to the outside. As such, the heater 330 directly heats wax in the wax reservoir 300a through the heat conductor 332 and also transfers heat to the nozzle 306 such that wax is prevented from being solidified near the discharging outlet of the nozzle during the work and such that in particular, the wax reservoir 300a as well as the nozzle 306 are kept to have a predetermined temperature only by heating wax in a degree not to spoil wax.

Also, as described above, the wax dispenser 300 may further comprise a charge button 308.

If a user pushes the charge button 308, the wax blocking ball 350 is moved away from the inlet 354 and then a liquid wax is introduced into the wax reservoir 300a through the nozzle 306 by suction. That is, when the wax reservoir 300a is contracted by the push of the press button unit 304, a negative pressure is generated in the wax reservoir 300a by an elastic force or restoration force of the wax reservoir 300a. At this time, the wax blocking ball 305 is pushed into the valve tube 351 by the push of the charge button 308 so that a liquid wax at the outside is introduced into the wax reservoir 300a by suction.

For this, as shown in FIGS. 17 and 18, the charge button 308 comprises a ball support rod 340 and a push button 342. The ball support rod 340 is arranged such that it moves forward or backward in the wax reservoir 300a and the ball support rod supports the wax blocking ball 350 during the forward movement to separate the wax blocking ball 350 from the inlet 354. In this case, the ball support rod 340 is inserted into an insertion hole 313 formed on the rear end of the wax reservoir 300a such that the front part of the ball support rod is disposed inside the wax reservoir 300a and the rear part of the ball support rod is disposed outside the wax reservoir 300a. While the ball support rod 340 is inserted into the insertion hole 313, it seals the insertion hole 313 to prevent air or wax in the wax reservoir 300a from leaking. The push button 342 engages with the rear end of the ball support rod 340 to move the ball support rod 340 forward by the push of the button. Therefore, the wax reservoir 300a draws in a liquid wax contained in the wax tank 12 through the nozzle 306 by a negative pressure and then contains it therein.

The preferred embodiments of the invention have been illustrated and explained herein. It will be apparent to those skilled in the art that various modifications and variations can be made in the present invention without departing from the spirit or scope of the invention. The scope of the present invention is not limited to the embodiments, but the embodiments are only exemplary. Therefore, the true scope of the present invention should be defined by the technical spirit of the appended claims and it is intended that the present invention cover modifications and variations of this invention provided they come within the scope of the appended claims and their equivalents.

Industrial Applicability

The invention fulfils industrial applicability since it relates to a wax dispenser for dental technology as well as a wax dispenser system using the same and it relates to a device for dental treatment.

The invention claimed is:

1. A wax dispenser for dental technology comprising:
a wax reservoir in the shape of a hollow tube which contains a liquid wax therein;
a nozzle which is disposed on the front end of the wax reservoir and which is in fluid communication with the wax reservoir;
a heater which heats wax to keep wax contained in the wax reservoir in liquid state;
an air-pressure supplier which increases the pressure in the wax reservoir by the introduction of air from the outside in a pressurization mode and decreases the pressure in the wax reservoir by the discharge of air to the outside in a depressurization mode; and
a dispenser actuator comprising a wax passage which allows the wax reservoir to be in fluid communication with the nozzle, and a passage open/shut device arranged to open and shut the wax passage to discharge wax contained in the wax reservoir through the nozzle in the pressurization mode and to introduce wax from the outside to the wax reservoir through the nozzle in the depressurization mode.

2. The wax dispenser according to claim 1, wherein the air-pressure supplier comprises:
an outer connection tube which is adapted to introduce air from the outside or to discharge air to the outside;
an inner connection tube which is disposed on the rear end of the wax reservoir and which is in fluid communication with the wax reservoir; and
an air passage which allows the outer connection tube to be in fluid communication with the inner connection tube.

3. The wax dispenser according to claim 2, further comprising:
a rear cap unit which opens and shuts the rear end of the inner connection tube to make the rear end of the inner connection tube opened or closed, wherein the air passage is disposed in the rear cap unit so that the outer connection tube is made to be in fluid communication with the inner connection tube when the rear cap unit closes the inner connection tube.

4. The wax dispenser according to claim 3, wherein the air-pressure supplier further comprises an air-pressure on/off valve which is adapted to connect the outer connection tube to the air passage and which is adapted to disconnect the outer connection tube from the air passage.

5. The wax dispenser according to claim 4, wherein the air-pressure on/off valve comprises:
a valve tube having a first communication hole which is in fluid communication with the air passage and a second communication hole which is in fluid communication with the outer connection tube;
an open/shut ball which is contained in the valve tube; and
a spring member which is adapted to press the open/shut ball to shut the first communication hole,
wherein the open/shut ball closes the first communication hole by the spring force of the spring member when the rear cap unit opens the rear end of the inner connection tube, and the open/shut ball is pressed against the spring force of the spring member by the inner connection tube when the rear cap unit closes the rear end of the inner connection tube such that the open/shut ball opens at least partially the first communication hole to allow the first communication hole to be in fluid communication with the air passage.

6. The wax dispenser according to claim 1, wherein the heater comprises:
a heating member which is disposed along the wax passage in the inner space of the wax reservoir; and
a heating sleeve which supplies power to the heating member such that the heating member generates heat.

7. The wax dispenser according to claim 6, wherein the heating member extends into the nozzle.

8. The wax dispenser according to claim 6, wherein the heating member is in the shape of a coil spring in the section where the heating member in the wax reservoir is located.

9. The wax dispenser according to claim 6, wherein the passage open/shut device comprises:
an elastic tube which constitutes at least part of the wax passage and which has an elastic contact portion, wherein the elastic contact portion constitutes an inner surface of the elastic tube which is at least partially in contact with an outer surface of the heating member penetrating the wax passage to shut the wax passage; and
a side button adapted to press and deform the elastic tube by the external manipulation of the side button such that the elastic contact portion is separated from the heating member and then the wax passage opens.

10. A wax dispenser system for dental technology comprising:
a wax dispenser for dental technology comprising;
a wax reservoir in the shape of a hollow tube which contains a liquid wax therein;
a nozzle which is disposed on the front end of the wax reservoir and which is in fluid communication with the wax reservoir;
a heater which heats wax to keep wax contained in the wax reservoir in liquid state;
an air-pressure supplier which increases the pressure in the wax reservoir by the introduction of air from the outside in a pressurization mode and decreases the pressure in the wax reservoir by the discharge of air to the outside in a depressurization mode; and
a dispenser actuator comprising a wax passage which allows the wax reservoir to be in fluid communication with the nozzle, and a passage open/shut device arranged to open and shut the wax passage to discharge wax contained in the wax reservoir through the nozzle in the pressurization mode and to introduce wax from the outside to the wax reservoir through the nozzle in the depressurization mode;
an air cable of which one end is connected to the air-pressure supplier of the wax dispenser for dental technology; and
air pumping unit which is connected to the other end of the air cable and which is adapted to discharge air to the air-pressure supplier or to suck air from the air-pressure supplier such that the air-pressure supplier operates in the pressurization mode or the depressurization mode.

11. The wax dispenser system according to claim 10, wherein the air pumping unit comprises:
an air pump which has a pumping discharge port for the discharge of air and a pumping suction port for the suction of air; and
a mode switching valve which selectively connects either the pumping discharge port or the pumping suction port to the air cable.

12. The wax dispenser. system according to claim 11, wherein the mode switching valve comprises:
a cable connection port which is connected to the air cable;
a discharge connection port which is connected to the pumping discharge port;
a suction connection port which is connected to the pumping suction port; and
a valve switch which operates either in a first switching position in which the cable connection port is connected to the discharge connection port for the operation of the air-pressure supplier in the pressurization mode or in a second switching position in which the cable connection port is connected to the suction connection port for the operation of the air-pressure supplier in the depressurization mode.

13. The wax dispenser system according to claim 12, wherein the mode switching valve further comprises a first dummy port and a second dummy port which are open to the outside respectively and independently; wherein the valve switch connects the suction connection port to the first dummy port when it operates in the first switching position and connects the discharge connection port to the second dummy port when it operates in the second switching position.

14. The wax dispenser system according to claim 12, wherein the air pumping unit further comprises a discharge air-pressure controller disposed on air line which connects the pumping discharge port to the discharge connection port so as to control the pressure of air which is discharged from the air pump.

15. The wax dispenser system according to claim 14, further comprising:
a suction air-pressure controller disposed on air line which connects the pumping suction port to the suction connection port so as to control the pressure of air which is introduced to the air pump.

16. The wax dispenser system according to claim 14, wherein at least one of the discharge air-pressure controller and the suction air-pressure controller is configured as an air pressure cylinder which temporarily contains air which is discharged from the air pump or air which is introduced to the air pump and then discharges or sucks air at a predetermined air pressure.

17. The wax dispenser system according to claim 10, further comprising:
- a power supply which supplies power for the heat generation of the heater in the wax dispenser for dental technology; and
- a power cable which connects the power supply to the heater,
- wherein the power cable extends in the air cable and is connected to the heater.

18. The wax dispenser system according to claim 17, further comprising:
- a main body which contains the air pumping unit therein;
- wherein the main body comprises an air connection port which is connected to the air pumping unit and a power connection port which is connected to the power supply;
- wherein the wax dispenser system further comprises a connection module which is disposed on the other side of the air cable and which has an air connection jack and a power connection jack, wherein the air connection jack is in fluid communication with the air cable and is connectable to the air connection port, and the power connection jack is electrically connected to the power cable disposed in the air cable and is connectable to the power connection port.

* * * * *